United States Patent
Laffend et al.

(10) Patent No.: US 7,629,161 B2
(45) Date of Patent: Dec. 8, 2009

(54) BIOCONVERSION OF A FERMENTABLE CARBON SOURCE TO 1,3-PROPANEDIOL BY A SINGLE MICROORGANISM

(75) Inventors: Lisa Anne Laffend, Claymont, DE (US); Vasantha Nagarajan, Wilmington, DE (US); Charles Edwin Nakamura, Claymont, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/589,485

(22) Filed: Oct. 30, 2006

(65) Prior Publication Data

US 2007/0048849 A1    Mar. 1, 2007

Related U.S. Application Data

(60) Division of application No. 09/575,638, filed on May 22, 2000, now Pat. No. 7,135,309, which is a division of application No. 08/849,404, filed as application No. PCT/US96/06705 on May 10, 1996, now abandoned, and a continuation-in-part of application No. 08/440,293, filed on May 12, 1995, now Pat. No. 5,686,276.

(51) Int. Cl.
| | |
|---|---|
| C12N 9/00 | (2006.01) |
| C12N 9/02 | (2006.01) |
| C12N 9/04 | (2006.01) |
| C12N 1/20 | (2006.01) |
| C07H 21/04 | (2006.01) |

(52) U.S. Cl. .................. 435/252.3; 435/183; 435/189; 435/190; 435/252.33; 536/23.2

(58) Field of Classification Search .............. 435/183, 435/189, 190, 252.3, 252.33; 536/23.2
See application file for complete search history.

(56) References Cited

FOREIGN PATENT DOCUMENTS

| | | |
|---|---|---|
| DE | 3734 764 | 10/1987 |
| EP | A-0 361 082 | 4/1990 |
| EP | 0 373 230 | 6/1990 |
| WO | WO-A-91 15590 | 10/1991 |
| WO | WO-A-93 25696 | 12/1993 |
| WO | WO 96/35796 A1 | 11/1996 |

OTHER PUBLICATIONS

Tong et al. Appl. Environ. Microbiol. Dec. 1991;57(12):3541-6).*
Gatenby et al. Accession AAV42012, Oct. 12, 1998.*
Dunn-Coleman et al. Accession AAV35743, Sep. 28, 1998.*
Chemical Abstracts, vol. 118, No. 7, Feb. 15, 1993, Daniel, Rolf et al., "Growth Temperature-Dependent Activity of Glycerol Dehydratase in *Escherichia coli* Expressingthe Citrobacter Freundii dha Regulon".
Chemical Abstracts, vol. 116, No. 9, Mar. 2, 1992, Tong, I Teh et al., "1,3-Propanediol Production by *Escherichia coli* Expressing Genes from the Klebsiella Pneumoniae dha Regulon".
Chemical Abstracts, vol. 120, No. 11, Mar. 14, 1994, Otto, Karin Elizabeth, "Cloning and Characterization of the Propanediol Dehydratase Genes in Salmonella Typhimurium".
Chemical Abstracts, vol. 118, No. 17, Apr. 26, 1993, Boenigk, Rainer et al., "Fermentation of Glycerol to 1,3-Propanediol in Continuous Cultures of Citrobacter Freundii".
Veiga da Cunba et al, *J. Bacteriol*, 174(3), 1013-1019 (1992).
Steib, M. et al, *Arch. Microbiol.*, 140, 139 146 (1984).
Tong, I-T. et al, *Appl. Biochem. Biotech*. 34/35, 149-159 (1992).
Tong, I-T., Ph.D., Thesis, University of Wisconsin-Madison (1992) (partial text submitted; full text provided upon request).
Daniel, R. et al, *J. of Bacteriology*, 177(8), 2151-2156 (1995).
Tobimatsu, T. et al, *J. Biolog. Chem.*, 270(13), 7142-7148 (1995).
Sobolov, M. et al, *J. of Bacteriology*, 79, 261-266 (1993).
Ruch, F.E. et al, *J. Bacteriol.*, 124(1), 348-352 (1975).
Talarico, T.L. et al., *Applied and Environmental Microbiology*, Apr. 1990, pp. 943-948.

* cited by examiner

*Primary Examiner*—Christian L Fronda

(57) ABSTRACT

A process is provided for the bioconversion of a carbon substrate to 1,3-propanediol by a single organism utilizing microorganisms containing the genes encoding for an active glycerol or diol dehydratase enzyme by contacting these organisms with a carbon substrate under the appropriate fermentation conditions.

8 Claims, 2 Drawing Sheets

BIOCONVERSION OF A FERMENTABLE CARBON SOURCE TO 1,3-PROPANEDIOL BY A SINGLE MICROORGANISM

This is a divisional application of U.S. application Ser. No. 09/575,638, filed 22 May 2000, issued as U.S. Pat. No. 7,135,309 on 14 Nov. 2006, which is a divisional of U.S. application Ser. No. 08/849,404, filed May 22, 1997, now abandoned, which is a 371 of PCT /US96/06705 filed on May 10, 1996 and a continuation-in-part of U.S. application Ser. No. 08/440,293 filed May 12, 1995, now U.S. Pat. No. 5,686,276.

FIELD OF INVENTION

This invention comprises a process for the bioconversion of a fermentable carbon source to 1,3-propanediol by a single microorganism.

BACKGROUND 1,3-Propanediol is a monomer having potential utility in the production of polyester fibers and the manufacture of polyurethanes and cyclic compounds.

A variety of chemical routes to 1,3-propanediol are known. For example ethylene oxide may be converted to 1,3-propanediol over a catalyst in the presence of phosphine, water, carbon monoxide, hydrogen and an acid, by the catalytic solution phase hydration of acrolein followed by reduction, or from hydrocarbons such as glycerol, reacted in the presence of carbon monoxide and hydrogen over catalysts having atoms from group VIII of the periodic table. Although it is possible to generate 1,3-propanediol by these methods, they are expensive and generate waste streams containing environmental pollutants.

It has been known for over a century that 1,3-propanediol can be produced from the fermentation of glycerol. Bacterial strains able to produce 1,3-propanediol have been found, for example, in the groups *Citrobacter, Clostridium, Enterobacter, Ilyobacter, Klebsiella, Lactobacillus*, and *Pelobacter*. In each case studied, glycerol is converted to 1,3-propanediol in a two step, enzyme catalyzed reaction sequence. In the first step, a dehydratase catalyzes the conversion of glycerol to 3-hydroxypropionaldehyde (3-HP) and water, Equation 1. In the second step, 3-HP is reduced to 1,3-propanediol by a NAD⁺-linked oxidoreductase, Equation 2. The 1,3-propanediol is not metabolized further and, as a result,

  (Equation 1)

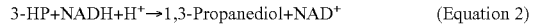  (Equation 2)

accumulates in high concentration in the media. The overall reaction consumes a reducing equivalent in the form of a cofactor, reduced β-nicotinamide adenine dinucleotide (NADH), which is oxidized to nicotinamide adenine dinucleotide (NAD⁺).

The production of 1,3-propanediol from glycerol is generally performed under anaerobic conditions using glycerol as the sole carbon source and in the absence of other exogenous reducing equivalent acceptors. Under these conditions, in e.g., strains of *Citrobacter, Clostridium*, and *Klebsiella*, a parallel pathway for glycerol operates which first involves oxidation of glycerol to dihydroxyacetone (DHA) by a NAD⁺- (or NADP⁺-) linked glycerol dehydrogenase, Equation 3. The DHA, following-phosphorylation to dihydroxyacetone phosphate (DHAP) by a DHA kinase (Equation 4),

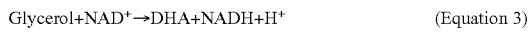  (Equation 3)

  (Equation 4)

becomes available for biosynthesis and for supporting ATP generation via e.g., glycolysis. In contrast to the 1,3-propanediol pathway, this pathway may provide carbon and energy to the cell and produces rather than consumes NADH.

In *Klebsiella pneumoniae* and *Citrobacter freundii*, the genes encoding the functionally linked activities of glycerol dehydratase (dhaB), 1,3-propanediol oxidoreductase (dhaT), glycerol dehydrogenase (dhaD), and dihydroxyacetone kinase (dhaK) are encompassed by the dha regulon. The dha regulons from *Citrobacter* and *Klebsiella* have been expressed in *Escherichia coli* and have been shown to convert glycerol to 1,3-propanediol.

Biological processes for the preparation of glycerol are known. The overwhelming majority of glycerol producers are yeasts but some bacteria, other fungi and algae are also known. Both bacteria and yeasts produce glycerol by converting glucose or other carbohydrates through the fructose-1,6-bisphosphate pathway in glycolysis or the Embden Meyerhof Parnas pathway, whereas, certain algae convert dissolved carbon dioxide or bicarbonate in the chloroplasts into the 3-carbon intermediates of the Calvin cycle. In a series of steps, the 3-carbon intermediate, phosphoglyceric acid, is converted to glyceraldehyde 3-phosphate which can be readily interconverted to its keto isomer dihydroxyacetone phosphate and ultimately to glycerol. Although biological methods of both glycerol and 1,3-propanediol production are known, it has never been demonstrated that the entire process can be accomplished by a single organism.

Neither the chemical nor biological methods described above for the production of 1,3-propanediol is well suited for industrial scale production since the chemical processes are energy intensive and the biological processes require the expensive starting material, glycerol. A method requiring low energy input and an inexpensive starting material is needed. A more desirable process would incorporate a microorganism that would have the ability to convert basic carbon sources such as carbohydrates or sugars to the desired 1,3-propanediol end-product.

Although a single organism conversion of fermentable carbon source other than glycerol or dihydroxyacetone to 1,3-propanediol would be desirable, it has been documented that there are significant difficulties to overcome in such an endeavor. For example, Gottschalk et al. (EP 373 230) teach that the growth of most strains useful for the production of 1,3-propanediol, including *Citrobacter freundii, Clostridium autobutylicum, Clostridium butylicum*, and *Klebsiella pneumoniae*, is disturbed by the presence of a hydrogen donor such as fructose or glucose. Strains of *Lacdobacillus brevis* and *Lactobacillus buchner*, which produce 1,3-propanediol in co-fermentations of glycerol and fructose or glucose, do not grow when glycerol is provided as the sole carbon source, and, although it has been shown that resting cells can metabolize glucose or fructose, they do not produce 1,3-propanediol. (Veiga DA Cunha et al., *J. Bacteriol.* 174, 1013 (1992)). Similarly, it has been shown that a strain of *Ilyobacter polytropus*, which produces 1,3-propanediol when glycerol and acetate are provided, will not produce 1,3-propanediol from carbon substrates other than glycerol, including fructose and glucose. (Steib et al., *Arch. Microbiol.* 140, 139 (1984)).

Finally Tong et al. (*Appl. Biochem. Biotech.* 34, 149 (1992)) has taught that recombinant *Escherichia coli* transformed with the dha regulon encoding glycerol dehydratase does not produce 1,3-propanediol from either glucose or xylose in the absence of exogenous glycerol.

Attempts to improve the yield of 1,3-propanediol from glycerol have been reported where co-substrates capable of providing reducing equivalents, typically fermentable sugars, are included in the process. Improvements in yield have been claimed for resting cells of *Citrobacter freundii* and *Klebsiella pneumoniae* DSM 4270 cofermenting glycerol and glucose (Gottschalk et al., supra.; and Tran-Dinh et al., DE 3734 764); but not for growing cells of *Klebsiella pneumoniae* ATCC 25955 cofermenting glycerol and glucose, which produced no 1,3-propanediol (1-T. Tong, Ph.D. Thesis, University of Wisconsin-Madison (1992)). Increased yields have been reported for the cofermentation of glycerol and glucose or fructose by a recombinant *Escherichia coli*; however, no 1,3-propanediol is produced in the absence of glycerol (Tong et al., supra.). In these systems, single organisms use the carbohydrate as a source of generating NADH while providing energy and carbon for cell maintenance or growth. These disclosures suggest that sugars do not enter the carbon stream that produces 1,3-propanediol. In no case is 1,3-propanediol produced in the absence of an exogenous source of glycerol. Thus the weight of literature clearly suggests that the production of 1,3-propanediol from a carbohydrate source by a single organism is not possible.

The problem to be solved by the present invention is the biological production of 1,3-propanediol by a single organism from an inexpensive carbon substrate such as glucose or other sugars. The biological production of 1,3-propanediol requires glycerol as a substrate for a two step sequential reaction in which a dehydratase enzyme (typically a coenzyme $B_{12}$-dependent dehydratase) converts glycerol to an intermediate, 3-hydroxypropionaldehyde, which is then reduced to 1,3-propanediol by a NADH- (or NADPH) dependent oxidoreductase. The complexity of the cofactor requirements necessitates the use of a whole cell catalyst for an industrial process which utilizes this reaction sequence for the production of 1,3-propanediol. Furthermore, in order to make the process economically viable, a less expensive feedstock than glycerol or dihydroxyacetone is needed. Glucose and other carbohydrates are suitable substrates, but, as discussed above, are known to interfere with 1,3-propanediol production. As a result no single organism has been shown to convert glucose to 1,3-propanediol.

Applicants have solved the stated problem and the present invention provides for bioconverting a fermentable carbon source directly to 1,3-propanediol using a single organism. Glucose is used as a model substrate and the bioconversion is applicable to any existing microorganism. Microorganisms harboring the gene for a dehydratase are able to convert glucose and other sugars through the glycerol degradation pathway to 1,3-propanediol with good yields and selectivities. Furthermore, the present invention may be generally applied to include any carbon substrate that is readily converted to 1) glycerol, 2) dihydroxyacetone, or 3) $C_3$ compounds at the oxidation state of glycerol (e.g., glycerol 3-phosphate) or 4) $C_3$ compounds at the oxidation state of dihydroxyacetone (e.g., dihydroxyacetone phosphate or glyceraldehyde 3-phosphate).

SUMMARY OF THE INVENTION

The present invention comprises a process for the bioconversion of a carbon substrate to 1,3-propanediol by a single microorganism having at least one gene capable of expressing a dehydratase enzyme by contacting said micro-organism with said substrate. The microorganism can be a wild-type, or genetically altered, such as a recombinant microorganism or a mutant of a microorganism. Preferably, the dehydratase enzyme is a glycerol dehydratase enzyme or a diol dehydratase enzyme.

The present invention further comprises the product of the above process.

The present invention further comprises a cosmid comprising a DNA fragment of about 35 kb isolated from *Klebsiella pneumoniae* wherein said fragment encodes an active glycerol dehydratase enzyme having the restriction digest in FIG. 1, columns 1 and 2. This cosmid, when transferred into a microorganism permits metabolism of a carbon substrate, in particular glucose, to 1,3-propanediol.

The present invention further comprises a transformed microorganism comprising a host microorganism and the above cosmid or any DNA fragment of said cosmid encoding an active functional protein other than a glycerol dehydratase enzyme.

The invention also encompasses a bioconversion process to produce 1,3-propanediol comprising contacting, under suitable conditions, glycerol with a single microorganism having at least one gene capable of expressing a dehydratase enzyme, the microorganism selected from the group consisting of members of the genera *Aspergillus, Saccharomyces, Zygosaccharomyces, Pichia, Kluyveromyces, Candida, Hansenula, Debaryomyces, Mucor, Torulopsis, Methylobacter, Salmonella, Bacillus, Streptomyces*, and *Pseudomonas*.

The invention also encompasses a bioconversion process to produce 1,3-propanediol comprising contacting, under suitable conditions, a carbon substrate with a single microorganism having at least one gene capable of expressing a dehydratase enzyme wherein the gene encodes glycerol dehydratase and is isolated from the group consisting of members of the genera *Klebsiella, Lactobacillus, Enterobacter, Citrobacter, Pelobacter, Ilyobacter*, and *Clostridium*.

The invention also encompasses a bioconversion process to produce 1,3-propanediol comprising contacting, under suitable conditions, a carbon substrate with a single microorganism having at least one gene capable of expressing a dehydratase enzyme wherein the gene encodes glycerol dehydratase and is isolated from the group consisting of members of the genera *Klebsiella*, and *Salmonella*.

Preferred host microorganisms are selected from the group consisting of members of the genera *Citrobacter, Enterobacter, Clostridium, Klebsiella, Aerobacter, Lactobacillus, Aspergillus, Saccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces* and *Pseudomonas*.

Recombinant microorganisms embodying the invention are set forth in the BRIEF DESCRIPTION OF THE BIOLOGICAL DEPOSITS.

BRIEF DESCRIPTION OF BIOLOGICAL DEPOSITS AND SEQUENCE LISTING

Figure 1:
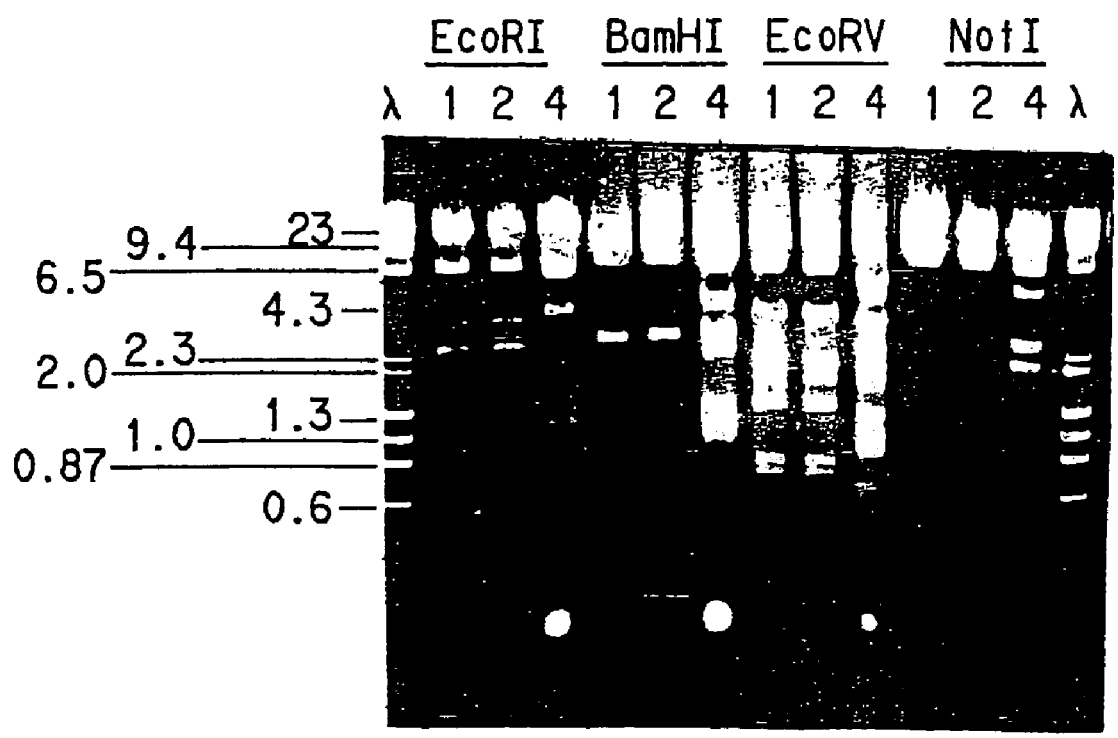
FIG. 1 shows restriction digests (EcoR 1, BamH 1, EcoR V and NotI) of cosmids pkP1, pKP2 and pKP4 labeled as columns 1, 2 and 4, respectively, and separation on a 0.8% agarose gel electrophoresis. Molecular size markers were loaded on the lanes in the end. Columns labeled as numbers 1 and 2 represent cosmids containing a glycerol dehydratase enzyme.
Figure 2:
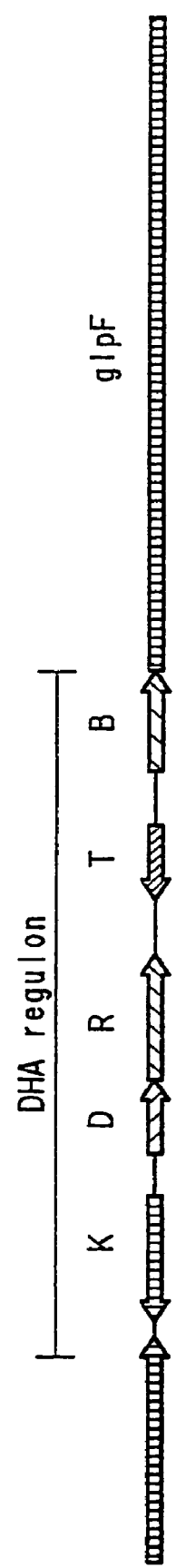
FIG. 2 shows a partial physical map of pKP1 and the position of the genes based on DNA sequence. The genes were identified based on comparison of deduced open reading frames with the Genbank data base using the Tfasta program provided by a sequence analysis software of the University of Wisconsin [Genetics Computer Group, Verison 7, April, 1991, 575 Science Drive, Madison, Wis. 53711].

The transformed *E. coli* DH5α containing cosmid pKP1 containing a portion of the *Kiebsiella* genome encoding the glycerol dehydratase enzyme was deposited on 18 Apr. 1995 with the ATCC under the terms of the Budapest Treaty and was designated ATCC 69789. The transformed *E.coli* DH5α containing cosmid pKP4 containing a portion of the *Kiebsiella* genome encoding a diol dehydratase enzyme was deposited on 18 Apr. 1995 with the ATCC under the terms of the Budapest Treaty and was designated ATCC 69790. The *Pseudomonas aeruginosa* strain PAO 2845: pDT9, transformed with a plasmid containing the dhaB operon was deposited on 11 Apr. 1996 with the ATCC under the terms of the Budapest Treaty and was designated ATCC 55760. The *Pichia pastoris* strain MSP42.81, transformed with non-replicative plasmids containing expression cassettes for the dhaB1, dhaB2, dhaB3 and dhaT genes, was deposited on 11 Apr. 1996 with the ATCC under the terms of the Budapest Treaty and was designated ATCC 74363. The *Saccharomyces cerevisiae*, strain pMCK1/10/17(HM)#A, transformed with a plasmid containing the dhaB1, dhaB2, dhaB3, and dhaT operon, was deposited before the filing of the instant international application, on May 9. 1996, with the ATCC under the terms of the Budapest Treaty and was designated ATCC 74370. The *Streptomyces lividans* strain SL/14.2, transformed with a plasmid containing the dhaB1, dhaB2, dhaB3, and dhaT operon, was deposited before the filing of the instant International application, on May 9, 1996, with the ATCC under the terms of the Budapest Treaty and was designated ATCC 98052. The *Bacillus licheniformis* strain BG188/pM26 (Clone #8), transformed with a plasmid containing the dhaB1, dhaB2 and dhaB3 operon, was deposited before the filing of the instant international application, on May 9, 1996, with the ATCC under the terms of the Budapest Treaty and was designated ATCC 98051. The *Bacillus subtilis* strain BG2864/pM27 (Clone #1), transformed with a plasmid containing the dhaB1, dhaB2, dhaB3 and dhaT operon, was deposited before the filing of the instant international application, on May 9, 1996, with the ATCC under the terms of the Budapest Treaty and was designated ATCC 98050. The *Aspergillus niger* strain TGR40-13, transformed with a plasmid containing the dhaB1, dhaB2, dhaB3 and dhaT operon, was deposited before the filing of the instant international application, on May 9, 1996, with the ATCC under the terms of the Budapest Treaty and was designated ATCC 74369. "ATCC" refers to the American Type Culture Collection international depository located at 10801 University Blvd., Manassas, Va. 20110-2209, U.S.A. The designations refer to the accession number of the deposited material.

Applicants have provided forty-six sequences in conformity with "Rules for the Standard Representation of Nucleotide and Amino Acid Sequences in Patent Applications" (Annexes I and II to the Decision of the President of the EPO, published in Supplement No. 2 to OJ EPO, 12/1992) and with 37 C.F.R 1.821-1.825 and Appendices A and B ("Requirements for Application Disclosures Containing Nucleotides and/or Amino Acid Sequences").

DETAILED DESCRIPTION OF THE INVENTION

The present invention provides a method for a biological production of 1,3-propanediol from a fermentable carbon source in a single organism. The method incorporates a microorganism containing a dehydratase enzyme which is contacted with a carbon substrate and 1,3-propanediol is isolated from the growth media The single organism may be a wild type organism or may be a genetically altered organism harboring a gene encoding a dehydratase enzyme.

The present method provides a rapid, inexpensive and environmentally responsible source of 1,3-propanediol monomer useful in the production of polyesters and other polymers.

As used herein the following terms may be used for interpretation of the claims and specification.

As used herein, the term "nucleic acid" refers to a large molecule which can be single-stranded or double-stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a plymer of DNA or RNA which can be single- or double-stranded, optionally containing synthetic, non-natural or altered nucleotide bases capable of incorporation into DNA or RNA polymers.

As used herein, "essentially similar" refers to DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that "essentially similar" sequences encompassed by this invention are also defined by their ability to hybridize, under stringent conditions (0.1×SSC, 0.1% SDS, 65° C.), with the sequences exemplified herein.

"Gene" refers to a nucleic acid fragment that expresses a specific protein, including regulatory sequences preceding (5' non-coding) and following (3' non-coding) the coding region.

"Native" or "wild-type" gene refers to the gene as found in nature with its own regulatory sequences.

The term "genetically altered or genetically altered microorganism" refers to any microorganism, suitable for use in the present invention, which has undergone an alteration of the native genetic machinery of the microorganism. Microorganisms may be genetically altered by undergoing transformation by vectors comprising heterologous nucleic acid fragments, mutagenesis with mutagenizing agents (e.g., UV light, ethanesulfonic acid) or any other method whereby stable alterations of the cell genome occur.

The term "construct" refers to a plasmid, virus, autonomously replicating sequence, genome integrating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "transformation" or "transfection" refers to the acquisition of new genes in a cell after the incorporation of nucleic acid. The acquired genes may be integrated into chromosomal DNA or introduced as extrachromosomal replicating sequences. The term "transformant" refers to the product of a transformation. The term "genetically altered" refers to the process of changing hereditary material by transformation or mutation.

The term "expression" refers to the transcription and translation to gene product from a gene coding for the sequence of the gene product.

The term "plasmid" or "vector" or "cosmid" as used herein refers to an extra chromosomal element often carrying genes which are not part of the central metabolism of the cell, and usually in the form of circular double-stranded DNA molecules.

The term "dehydratase enzyme" will refer to any enzyme that is capable of isomerizing or converting a glycerol molecule to the product 3-hydroxypropionaldehyde. For the purposes of the present invention the dehydratase enzymes include a glycerol dehydratase and a diol dehydratase having preferred substrates of glycerol and 1,2-propanediol, respectively.

The term "carbon substrate" or "carbon source" means any carbon source capable of being metabolized by a microorganism wherein the substrate contains at least one carbon atom, provided that the carbon substrate is other than glycerol or dihydroxyacetone.

Construction of Recombinant Organisms:

Recombinant organisms containing the necessary genes that will encode the enzymatic pathway for the conversion of a carbon substrate to 1,3-propanediol may be constructed using techniques well known in the art. In the present invention genes encoding dehydratase enzyme were isolated from a native host such as *Klebsiella* and used to transform the *E. coli* host strains DH5α, ECL707 and AA200.

Methods of obtaining desired genes from a bacterial genome are common and well known in the art of molecular biology. For example, if the sequence of the gene is known, suitable genomic libraries may be created by restriction endonuclease digestion and May be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively, cosmid libraries may be created where large segments of genomic DNA (35-45 kb) may be packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook, J. et al., *Molecular Cloning: A Laboratory Manual*, Second Edition (1989) Cold Spring Harbor Laboratory Press, herein incorporated by reference.

Typically to clone cosmids, foreign DNA is isolated and ligated, using the appropriate restriction endonucleases, adjacent to the cos region of the cosmid vector. Cosmid vectors containing the linearized foreign DNA is then reacted with a DNA packaging vehicle such as bacteriophage λ. During the packaging process the cos sites are cleaved and the foreign DNA is packaged into the head portion of the bacterial viral particle. These particles are then used to transfect suitable host cells such as *E. coli*. Once injected into the cell, the foreign DNA circularizes under the influence of the cos sticky ends. In this manner large segments of foreign DNA can be introduced and expressed in recombinant host cells.

Cosmid vectors and cosmid transformation methods were used within the context of the present invention to clone large segments of genomic DNA from bacterial genera known to possess genes capable of processing glycerol to 1,3-propanediol. Specifically, genomic DNA from *K. pneumoniae* was isolated by methods well known in the art and digested with the restriction enzyme Sau3A for insertion into a cosmid vector Supercos 1™ and packaged using GigapackII packaging extracts. Following construction of the vector *E. coli* XL1-Blue MR cells were transformed with the cosmid DNA. Transformants were screened for the ability to convert glycerol to 1,3-propanediol by growing the cells in the presence of glycerol and analyzing the media for 1,3-propanediol formation.

Two of the 1,3-propanediol positive transformants were analyzed and the cosmids were named pKP1 and pKP2. DNA sequencing revealed extensive homology to the glycerol dehydratase gene from *C. freundii*, demonstrating that these transformants contained DNA encoding the glycerol dehydratase gene. Other 1,3-propanediol positive transformant were analyzed and the cosmids were named pKP4 and pKP5. DNA sequencing revealed that these cosmids carried DNA encoding a diol dehydratase gene.

Although the instant invention utilizes the isolated genes from within a *Klebsiella* cosmid, alternate sources of dehydratase genes include, but are not limited to, *Citrobacter*, *Clostridia*, and *Salmonella*.

Other genes that will positively affect the production of 1,3-propanediol may be expressed in suitable hosts. For example it may be highly desirable to over-express certain enzymes in the glycerol degradation pathway and/or other pathways at levels far higher than currently found in wild type cells. This may be accomplished by the selective cloning of the genes encoding those enzymes into multicopy plasmids or placing those genes under a strong inducible or constitutive promoter. Methods for over-expressing desired proteins are common and well known in the art of molecular biology and examples may be found in Sambrook, supra. Furthermore, specific deletion of certain genes by methods known to those skilled in the art will positively affect the production of 1,3-propanediol. Examples of such methods can be found in Methods in Enzymology, Volume 217, R. Wu editor, Academic Press:San Diego (1993).

Mutants:

In addition to the cells exemplified it is contemplated that the present method will be able to make use of cells having single or multiple mutations specifically designed to enhance the production of 1,3-propanediol. Cells that normally divert a carbon feed stock into non-productive pathways, or that exhibit significant catabolite repression could be mutated to avoid these phenotypic deficiencies. For example, many wild type cells are subject to catabolite repression from glucose and by-products in the media and it is contemplated that mutant strains of these wild type organisms, capable of 1,3-propanediol production that are resistant to glucose repression, would be particularly useful in the present invention.

Methods of creating mutants are common and well known in the art. For example, wild type cells may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible but are generally not as effective as the short wave UV light unless used in conjunction with various activators such as psoralen dyes that interact with the DNA.

Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See Brock, Supra., DeMancilha et al., *Food Chem.*, 14, 313, (1984).

Mutations and Transformations in the 1,3-propanediol Production Pathway:

Representative enzyme pathway. The production of 1,3-propanediol from glucose can be accomplished by the following series of steps. This series is representative of a number of pathways known to those skilled in the art. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or reduction of DHAP to glycerol 3-phosphate (G3P) followed by hydrolysis. The hydrolysis step can be catalyzed by any number of cellular phosphatases which are known to be non-specific with respect to their substrates or the activity can be introduced into the host by recombination. The reduction step can be catalyzed by a $NAD^+$ (or $NADP^+$) linked host enzyme or the activity can be introduced into the host by recombination. It is notable that the dha regulon contains a glycerol dehydrogenase (E.C. 1.1.1.6) which catalyzes the reversible reaction of Equation 3.

Glycerol→3-HP+$H_2O$ (Equation 1)

3-HP+NADH+$H^+$→1,3-Propanediol+$NAD^+$ (Equation 2)

Glycerol+$NAD^+$→DHA+NADH+$H^+$ (Equation 3)

Glycerol is converted to 1,3-propanediol via the intermediate 3-hydroxypropionaldehye (3-HP) as has been described in detail above. The intermediate 3-HP is produced from glycerol, Equation 1, by a dehydratase enzyme which can be encoded by the host or can introduced into the host by recombination. This dehydratase can be glycerol dehydratase (E.C. 4.2.1.30), diol dehydratase (E.C. 4.2.1.28) or any other enzyme able to catalyze this transformation. Glycerol dehydratase, but not diol dehydratase, is encoded by the dha regulon. 1,3-Propanediol is produced from 3-HP, Equation 2, by a $NAD^+$- (or $NADP^+$) linked host enzyme or the activity can introduced into the host by recombination. This final reaction in the production of 1,3-propanediol can be catalyzed by 1,3-propanediol dehydrogenase (E.C. 1.1.1.202) or other alcohol dehydrogenases.

Mutations and transformations that affect carbon channeling. A variety of mutant organisms comprising variations in the 1,3-propanediol production pathway will be useful in the present invention. For example the introduction of a triose-phosphate isomerase mutation (tpi-) into the microorganism of the present invention is an example of the use of a mutation to improve the performance by carbon channeling. The mutation can be directed toward a structural gene so as to impair or improve the activity of an enzymatic activity or can be directed toward a regulatory gene so as to modulate the expression level of an enzymatic activity.

Alternatively, transformations and mutations can be combined so as to control particular enzyme activities for the enhancement of 1,3-propanediol production. Thus it is within the scope of the present invention to anticipate modifications of a whole cell catalyst which lead to an increased production of 1,3-propanediol.

Media and Carbon Substrates:

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. Glycerol production from single carbon sources (e.g., methanol, formaldehyde or formate) has been reported in methylotrophic yeasts (K. Yamada et al., *Agric. Biol. Chem.*, 53(2) 541-543, (1989))

and in bacteria (Hunter et. al., *Biochemistry*, 24, 4148-4155, (1985)). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York (1986)). The ribulose monophosphate pathway involves the condensation of formate with ribulose-5-phosphate to form a 6 carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* (1990), 153(5), 485-9). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, sucrose or methanol.

In addition to an appropriate carbon source, fermentation media must contain suitable minerals, salts, cofactors, buffers and other components, known to those skilled in the art, suitable for the growth of the cultures and promotion of the enzymatic pathway necessary for 1,3-propanediol production. Particular attention is given to Co(II) salts and/or vitamin $B_{12}$ or precursors thereof.

Culture Conditions:

Typically cells are grown at 30° C. in appropriate media. Preferred growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate, may also be incorporated into the reaction media Similarly, the use of agents known to modulate enzymatic activities (e.g., methyl viologen) that lead to enhancement of 1,3-propanediol production may be used in conjunction with or as an alternative to genetic manipulations.

Suitable pH ranges for the fermentation are between pH 5.0 to pH 9.0 where pH 6.0 to pH 8.0 is preferred as the initial condition.

Reactions may be performed under aerobic or anaerobic conditions where anaerobic or microaerobic conditions are preferred.

Batch and Continuous Fermentations:

The present process employs a batch method of fermentation. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1,3-propanediol production.

Identification and Purification of 1,3-propanediol:

Methods for the purification of 1,3-propanediol from fermentation media are known in the art. For example propanediols can be obtained from cell media by subjecting the reaction mixture to extraction with an organic solvent, distillation and column chromatography (U.S. Pat. No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. Preferred in the present invention is a method where fermentation media is analyzed on an analytical ion exchange column using a mobile phase of 0.01N sulfuric acid in an isocratic fashion.

Cells:

Cells suitable in the present invention comprise those that harbor a dehydratase enzyme. It is contemplated that suitable cells may be either prokaryotic or eukaryotic and will be limited only by their ability to express an active dehydratase enzyme. Particularly useful in the present invention will be cells that are readily adaptable to large-scale fermentation methods. Such organisms are well known in the art of industrial bioprocessing, examples of which may be found in "Recombinant Microbes for Industrial and Agricultural Applications", Murooka et al., eds., Marcel Dekker, Inc., New York, N.Y. (1994), and include fermentative bacteria as well as yeast and filamentous fingi. Typically the enzyme will be either a glycerol dehydratase or a diol dehydratase having a substrate specificity for either glycerol or 1,2-propanediol, respectively. Dehydratase enzymes are capable of converting glycerol to hydroxypropionaldehyde (3-HPA) which is then converted to 1,3-propanediol. Cells containing this pathway may include mutated or recombinant organisms belonging to the genera *Citrobacter, Enterobacter, Clostridium, Klebsiella, Samonella*, and *Lactobacillus*. Microorganisms known by persons skilled in the art to produce glycerol by fermentation, e.g., *Aspergillus, Saccharomyces, Zygosaccharomyces, Pichia, Kluyveromyces, Candida, Hansenula, Dunaliella, Debaryomyces, Miucor, Torylopsis*, and *Methylobacteria*, may be the hosts for a recombinant dehydratase enzyme. Other cells suitable as hosts in the present invention include *Bacillus, Escherichia, Pseudomonas* and *Streptomyces*. While not wishing to be bound by theory, it is believed that organisms, belonging to the above mentioned groups, exist in nature that are suitable for the present invention.

On the basis of applicants' experimental work it is contemplated that a wide variety of cells may be used in the present invention. Applicants have demonstrated for example that cells varying widely in genetic and phenotypic composition are able to bioconvert a suitable carbon substrate to 1,3-propanediol. Cells exemplified include: a *K. pneumoniae* mutant strain constitutive for the dha genes, recombinant *E. coli* strains comprising elements of the *Klebsiella* genome containing genes encoding either glycerol or diol dehydratase, and recombinant *E. coli* (tpi$^-$) strains also transfected with elements of the *Klebsiella* genomes and harboring a mutation in the gene encoding the triosephosphate isomerase enzyme.

Although *E. coli* transformants containing the dha regulon from *Klebsiella pneumonia* were able to convert glycerol to 1,3-propanediol even in the presence of glucose or xylose (Tong et al., *Appl. Biochem. Biotech.*, 34, 149 (1992)) no 1,3-propanediol was detected by these organisms in the presence of glucose alone. In direct contrast to this disclosure, applicants have discovered that three strains of *E. coli*, containing either of two independently isolated cosmids comprising the dha regulon from *Klebsiella pneumonia*, produced 1,3-propanediol from a feed of glucose with no exogenously added glycerol present. *E. coli* strain ECL707, containing cosmid vectors pKP-1 or pKP-2 comprising the *K. pneumoniae* dha regulon, showed detectable though modest production of 1,3-propanediol from glucose in the absence of exogenously added glycerol, (Example 4). Recombinant *E. coli* strains constructed from an alternate host organism, DH5α, also containing cosmid vectors pKP-1 or pKP-2, were found to be more effective than the ECL707 recombinants in producing 1,3-propanediol from glucose under the appropriate conditions, (Example 3). Most effective in producing 1,3-propanediol from glucose under the conditions of Example 4 were the recombinant *E. coli* strains AA200 containing cosmid vectors pKP-1 or pKP-2, Example 2. *E. coli* strain AA200 contains a defective triosephosphate isomerase enzyme (tpi$^-$).

A strain of AA200-pKP1, selected for further study from a pool of independent isolates from the transformation reaction, converted glucose to 1,3-propanediol in a two stage reaction. In the first stage, the strain AA200-pKP1-5 was grown to high cell density in the absence of glucose and glycerol. In the second stage, the grown cells, suspended in a medium containing glucose but no glycerol, converted glucose to 1,3-propanediol with high conversion and selectivity, Example 5. Although differing immunochemically, chromatographically, and genetically, the coenzyme $B_{12}$-dependent enzymes glycerol dehydratase (E.C. 4.2.1.30) and diol dehydratase (E.C. 4.2.1.28) catalyze the conversion of glycerol to 3-hydroxypropionaldehyde. Glycerol dehydratase, but riot diol dehydratase, is encompassed by the dha regulon. *K pneumoniae* ATCC 8724, containing a diol dehydratase but not a glycerol dehydratase converts glycerol to 1,3-propanediol (Forage et al., *J. Bacteriol.*, 149, 413, (1982)). Recombinant *E. coli* strains ECL707 and AA200, containing cosmid vector pKP4 encoding genes for a diol dehydratase, converted glucose to 1,3-propanediol, Example 2 and Example 4.

*K. pneumoniae* ECL2106, prepared by mutagenesis from a naturally occurring strain (Ruch et al., *J. Bacteriol.* 124, 348 (1975)), exibits constitutive expression of the dha regulon (Ruch et al., supra; Johnson et al., *J. Bacteriol.* 164, 479 (1985)). A strain derived from *K. pneumoniae* ATCC 25955, displaying the same phenotype, has been similarly prepared (Forage et al., *J. Bacteriol.* 149, 413 (1982)). Expression of the *Klebsiella* dha structural genes is, in part, controlled by a repressor (product of dha R) (Sprenger et al., *J. Gen Microbiol.* 135, 1255 (1989)). Applicants have shown that ECL2106, which is constitutive for the dha structural genes, produced 13-propanediol from a feed of glucose in the absence of exogenously added glycerol, Example 6. This is in contrast to wild type *K. pneumoniae* ATCC 25955 which did not produce detectable levels of 1,3-propanediol under the same conditions, Example 6.

The expression of the dha structural genes in ECL2106 is further controlled by catabolite expression (Sprenger et al., *J. Gen Microbiol.* 135, 1255 (1989)). Elimination of catabolite repression can be achieved by placing the necessary structural genes under the control of alternate promoters as has been demonstrated for 1,3-propanediol oxidoreductase (dhaT) from *C. freundii* and diol dehydratase from *K. oxytoca* ATCC 8724 (Daniel et al., *J. Bacteriol.* 177, 2151 (1995) and Tobimatsu et al., *J. Biol. Chem.* 270, 7142 (1995)). By eliminating catabolite repression from ECL2106 in this manner, an improvement in the production of 1,3-propanediol from glucose in the absence of an exogenous source of glycerol is achieved. An even further improvement is obtained by appropriate carbon channelling as is described, by example, with the tpi$^-$ mutation.

As the dha regulons of *Citrobacter* and *Klebsiella* sp. are strikingly similar, one of skill in the art will appreciate that teachings that involve the production of 1,3-propanediol from glucose in the absence of an exogenous source of glycerol for *Klebsiella* sp. applies to *Citrobacter* sp. as well. Furthermore, as the metabolism of glycerol by *C. butyricum* is comparable to that of *K. pneumoniae* [Zeng et al., *Biotechnol. and Bioeng.* 44, 902 (1994)], teachings will extend to *Clostridia* sp. as well.

EXAMPLES

General Methods

Procedures for phosphorylations, ligations and transformations are well known in the art. Techniques suitable for use in the following examples may be found in Sambrook, J. et al., *Molecular Cloning: A Laboratory Manual*, Second Edition, Cold Spring Harbor Laboratory Press (1989).

Materials and methods suitable for the maintenance and growth of bacterial cultures are well known in the art. Techniques suitable for use in the following examples may be found in *Manual of Methods for General Bacteriology* (Phillipp Gerhardt, R G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters, 50 amp is 50 µg/mL ampicillin, and LE-50 amp is Luria-Bertani broth containing 50 µg/mL ampicillin.

Within the tables the following abreviations are used. "Con." is conversion, "Sel." is selectivity based on carbon, and "nd" is not detected.

Enzyme Assays

Glycerol dehydratase activity in cell free extracts was determined using 1,2-propanediol as substrate. The assay, based on the reaction of aldehydes with methylbenzo-2-thiazolone hydrazone, has been described by Forage and Foster (*Biochim. Biophys. Acta*, 569, 249 (1979)). The activity of 1,3-propanediol oxidoreductase, sometimes referred to as 1,3-propanediol dehydrogenase, was determined in solution or in slab gels using 1,3-propanediol and NAD$^+$ as substrates as has also been described. Johnson and Lin, *J. Bacteriol.*, 169, 2050 (1987).

Isolation and Identification 1,3-propanediol

The conversion of glycerol to 1,3-propanediol was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 N H$_2$SO$_4$ as mobile phase at a flow rate of 0.5 ml/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of 1,3-propanediol was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated were compared to that of authentic 1,3-propanediol (m/e: 57, 58).

An alternative method for GC/MS involved derivatization of the sample. To 1.0 mL of sample (e.g., culture supernatant) was added 30 uL of concentrated (70% v/v) perchloric acid. After mixing, the sample was frozen and lyophilized. A 1:1 mixture of bis(trimethylsilyl)trifluoroacetamide:pyridine (300 uL) was added to the lyophilized material, mixed vigorously and placed at 65° C. for one h. The sample was clarified of insoluble material by centrifugation. The resulting liquid partitioned into two phases, the upper of which was used for analysis. The sample was chromatographed on a DB-5 column (48 m, 0.25 mm I.D., 0.25 um film thickness; from J&W Scientific) and the retention time and mass spectrum of the 1,3-propanediol derivative obtained from culture supernatants were compared to that obtained from authentic standards. The mass spectra of TMS-derivatized 1,3-propanediol contains the characteristic ions of 205, 177, 130 and 115 AMU.

Construction of *K. Pneumoniae* Cosmid Libraries

*K. pneumoniae* (ATCC 25955) was grown in 100 mL LB medium for 8 h at 37° C. with aeration. Bacteria (25 mL per tube) were centrifuged at 3,000 rpm for 15 min in a DuPont Sorvall GLC 2.B centrifuge at room temperature. The bacteria were pelleted and supernatant was decanted. The bacterial cell pellet was frozen at −20° C. The chromosomal DNA was isolated as outlined below with special care taken to avoid shearing of DNA (i.e., vortexing was avoided). One tube of bacteria was resuspended in 2.5 mL of 50 mM Tris-10 mM EDTA and 500 µL of lysozyme (1 mg/mL) was added. The pellet was gently resuspended and the suspension was incubated at 37° C. for 15 min. Sodium dodecyl sulfate was added to bring the final concentration to 0.5%. This resulted in the solution becoming clear. Proteinase K (50 ug/mL) was added and the suspension was incubated at 55° C. for 2 h. The tube was removed and transferred to an ice bath and sodium chloride was added to yield a 0.4 M final concentration. Two volumes of ethanol were added to the liquid. A glass tube was inserted to the interface and the DNA was gently spooled. DNA was dipped into a tube containing 70% ethanol. After drying in vacuo, the DNA was resuspended in 500 ul of water and the concentration of DNA was determined spectrophotometrically. A diluted aliquot of DNA was run on a 0.5% agarose gel to determine the intact nature of DNA.

The chromosomal DNA was partially digested with Sau3A as outlined by Sambrook et al., supra. DNA (2 ug) was digested with 2 units of Sau3A (Promega, Madison, Wis.) at room temperature in 200 µL of total volume. At 0, 5, 10 and 20 min, samples (50 µL) were removed and transferred to tubes containing 5 mmol of EDTA These tubes were incubated at 70° C. for 10 min. An aliquot (2 µL) was withdrawn and analyzed on a 0.5% agarose gel electrophoresis to determine the level of digestion and the rest of the sample (48 µL) was stored at −20° C. The gel was stained with ethidium bromide and visualized under UV to determine the partial digestion of the chromosomal DNA. A decrease in the size of the chromosomal DNA with increase in time was observed showing that the decrease in the size of the chromosomal DNA is due to the action of Sau3A. DNA was extracted from rest of the sample by standard protocol methods (Sambrook et al., supra).

A cosmid library of partially digested DNA from *K. pneumoniae* was prepared using Supercos cosmid vector kit and GigapackII packaging extracts using reagents purchased from Stratagene (La Jolla, Calif.). The instructions provided by the manufacturer were followed. The packaged *K. pneumoniae* contained $4 \times 10^4$ to $1.0 \times 10^5$ phage titer as determined by transfecting *E. coli* XL1-Blue MR.

Cosmid DNA was isolated from 6 of the *E. coli* transformants and found to contain large insert of DNA (25 to 30 kb).

Example 1

Cloning and Transformation of *E. coli* Host Cells with Cosmid DNA for the Expression of 1,3-propanediol Media Synthetic S12 medium was used in the screening of bacterial transformants for the ability to make 1,3-propanediol. S12 medium contains: 10 mM ammonium sulfate, 50 mM potassium phosphate buffer, pH 7.0, 2 mM $MgCl_2$, 0.7 mM $CaCl_2$, 50 µM $MnCl_2$, 1 µM $FeCl_3$, 1 µM ZnCl, 1.7 µM $CuSO_4$, 2.5 µM $CoCl_2$, 2.4 µM $Na_2MoO_4$, and 2 µM thiamine hydrochloride.

Medium A used for growth and fermentation consisted of: 10 mM ammonium sulfate; 50 mM MOPS/KOH buffer, pH 7.5; 5 mM potassium phosphate buffer, pH 7.5; 2 mM $MgCl_2$; 0.7 mM $CaCl_2$; 50 µM $MnCl_2$; 1 µM $FeCl_3$; 1 µM ZnCl; 1.72 µM $CuSO_4$; 2.53 µM $CoCl_2$; 2.42 µM $Na_2MoO_4$; 2 µM thiamine hydrochloride; 0.01% yeast extract; 0.01% casamino acids; 0.8 µg/mL vitamin $B_{12}$; and 50 amp. Medium A was supplemented with either 0.2% glycerol or 0.2% glycerol plus 0.2% D-glucose as required.

Cells:

*Klebsiella pneumoniae* ECL2106 (Ruch et al., *J. Bacteriol.*, 124, 348 (1975)), also known in the literature as *K. aerogenes* or *Aerobacter aerogenes*, was obtained from E. C. C. Lin (Harvard Medical School, Cambridge, Mass.) and was maintained as a laboratory culture.

*Klebsiella pneumoniae* ATCC 25955 was purchased from American Type Culture Collection (Rockville, Md.).

*E. coli* DH5α was purchased from Gibco/BRL and was transformed with the cosmid DNA isolated from *Klebsiella pneumoniae* ATCC 25955 containing a gene coding for either a glycerol or diol dehydratase enzyme. Cosmids containing the glycerol dehydratase were identified as pKP1 and pKP2 and cosmid containing the diol dehydratase enzyme were identified as pKP4. Transformed DH5α cells were identified as DH5α-pKP1, DH5α-pKP2, and DH5α-pKP4.

*E. coli* ECL707 (Sprenger et al., *J. Gen. Microbiol.*, 135, 1255 (1989)) was obtained from E. C. C. Lin (Harvard Medical School, Cambridge, Mass.) and was similarly transformed with cosmid DNA from *Klebsiella pneumoniae*. These transformants were identified as ECL707-pKP1 and ECL707-pKP2, containing the glycerol dehydratase gene and ECL707-pKP4 containing the diol dehydratase gene.

*E. coli* AA200 containing a mutation in the tpi gene (Anderson et al., *J. Gen Microbiol.*, 62, 329 (1970)) was purchased from the *E. coli* Genetic Stock Center, Yale University (New Haven, Conn.) and was transformed with *Klebsiella* cosmid DNA to give the recombinant organisms AA200-pKP1 and AA200-pKP2, containing the glycerol dehydratase gene, and AA200-pKP4, containing the diol dehydratase gene.

DH5α:

Six transformation plates containing approximately 1,000 colonies of *E. coli* XL1-Blue MR transfected with *K. pneumoniae* DNA were washed with 5 mL LB medium and centrifuged. The bacteria were pelleted and resuspended in 5 mL LB medium+glycerol. An aliquot (50 µL) was inoculated into a 15 mL tube containing S12 synthetic medium with 0.2% glycerol+400 ng per mL of vitamin $B_{12}$+0.001% yeast extract+50 amp. The tube was filled with the medium to the top and wrapped with parafilm and incubated at 30° C. A slight turbidity was observed after 48 h. Aliquots, analyzed for product distribution as described above at 78 h and 132 h, were positive for 1,3-propanediol, the later time points containing increased amounts of 1,3-propanediol.

The bacteria, testing positive for 1,3-propanediol production, were serially diluted and plated onto LB-50 amp plates in order to isolate single colonies. Forty eight single colonies were isolated and checked again for the production of 1,3-propanediol. Cosmid DNA was isolated from 6 independent clones and transformed into *E. coli* strain DH5α. The transformants were again checked for the production of 1,3-propanediol. Two transformants were characterized further and designated as DH5α-pKP1 and DH5α-pKP2.

A 12.1 kb EcoRI-SalI fragment from pKP1, subcloned into pIBI31 (IBI Biosystem, New Haven, Conn.), was sequenced and termed pHK28-26 (SEQ ID NO:1). Sequencing revealed the loci of the relevant open reading frames of the dha operon encoding glycerol dehydratase and genes necessary for regulation. Referring to SEQ ID NO:1, a fragment of the open reading frame for dhaK encoding dihydroxyacetone kinase is found at bases 1-399; the open reading frame dhaD encoding glycerol dehydrogenase is found at bases 983-2107; the open reading frame dhaR encoding the repressor is found at bases 22094134; the open reading frame dhaT encoding 1,3-propanediol oxidoreductase is found at bases 5017-6180; the open reading frame dhaB1 encoding the alpha subunit glycerol dehydratase is found at bases 7044-8711; the open reading frame dhaB2 encoding the beta subunit glycerol dehydratase is found at bases 8724-9308; the open reading frame dhaB3 encoding the gamma subunit glycerol dehydratase is found at bases 9311-9736; and the open reading frame dhaBX, encoding a protein of unknown function is found at bases 9749-11572.

Single colonies of *E. coli* XL1-Blue MR transfected with packaged cosmid DNA from *K. pneumoniae* were inoculated into microtiter wells containing 200 uL of S15 medium (ammonium sulfate, 10 mM; potassium phosphate buffer, pH 7.0, 1 mM; MOPS/KOH buffer, pH 7.0, 50 mM; $MgCl_2$, 2 mM; $CaCl_2$, 0.7 mM; $MnCl_2$, 50 uM; $FeCl_3$, 1 uM; ZnCl, 1 uM; $CuSO_4$, 1.72 uM; $CoCl_2$, 2.53 uM; $Na_2MoO_4$, 2.42 uM; and thiamine hydrochloride, 2 uM)+0.2% glycerol+400 ng/mL of vitamin $B_{12}$+0.001% yeast extract+50 ug/mL ampicillin. In addition to the microtiter wells, a master plate containing LB-50 amp was also inoculated. After 96 h, 100 uL was withdrawn and centrifuged in a Rainin microfuge tube containing a 0.2 micron nylon membrane filter. Bacteria were retained and the filtrate was processed for HPLC analysis. Positive clones demonstrating 1,3-propanediol production were identified after screening approximately 240 colonies. Three positive clones were identified, two of which had grown on LB-50 amp and one of which had not. A single colony, isolated from one of the two positive clones grown on LB-50 amp and verified for the production of 1,3-propanediol, was designated as pKP4. Cosmid DNA was isolated from E. coli strains containing pKP4 and E. coli strain DH5α was transformed. An independent transformant, designated as DH5α-pKP4, was verified for the production of 1,3-propanediol.

ECL707:

E. coli strain ECL707 was transformed with cosmid K. pneumoniae DNA corresponding to pKP1, pKP2, pKP4 and the Supercos vector alone and named ECL707-pKP1, ECL707-pKP2, ECL707-pKP4, and ECL707-sc, respectively. ECL707 is defective in glpK, gld, and ptsD which encode the ATP-dependent glycerol kinase, NAD$^+$-linked glycerol dehydrogenase, and enzyme II for dihydroxyacetone of the phosphoenolpyruvate dependent phosphotransferase system, respectively.

Twenty single colonies of each cosmid transformation and five of the Supercos vector alone (negative control) transformation, isolated from LB-50 amp plates, were transferred to a master LB-50 amp plate. These isolates were also tested for their ability to convert glycerol to 1,3-propanediol in order to determine if they contained dehydratase activity. The transformants were transferred with a sterile toothpick to microtiter plates containing 200 μL of Medium A supplemented with either 0.2% glycerol or 0.2% glycerol plus 0.2% D-glucose. After incubation for 48 hr at 30° C., the contents of the microtiter plate wells were filtered through an 0.45μ nylon filter and chromatographed by HPLC. The results of these tests are given in Table 1.

TABLE 1

Conversion of glycerol to 1,3-propanediol by transformed ECL707: number of positive isolates/number of isolates tested

| Transformant | Glycerol | Glycerol plus Glucose |
|---|---|---|
| ECL707-pKP1 | 19/20 | 19/20 |
| ECL707-pKP2 | 18/20 | 20/20 |
| ECL707-pKP4 | 0/20 | 20/20 |
| ECL707-sc | 0/5 | 0/5 |

AA200:

E. coli strain AA200 was transformed with cosmid K. pneumoniae DNA corresponding to pKP1, pKP2, pKP4 and the Supercos vector alone and named AA200-pKP1, AA200-pKP2, AA200-pKP4, and AA200-sc, respectively. Strain AA200 is defective in triosephosphate isomerase, (tpi$^-$).

Twenty single colonies of each cosmid transformation and five of the empty vector transformation were isolated and tested for their ability to convert glycerol to 1,3-propanediol as described for E. coli strain ECL707. The results of these tests are given in Table 2.

TABLE 2

Conversion of glycerol to 1,3-propanediol by transformed AA200: Number of positive isolates/number of isolates tested

| Transformant | Glycerol | Glycerol plus Glucose |
|---|---|---|
| AA200-pKP1 | 17/20 | 17/20 |
| AA200-pKP2 | 17/20 | 17/20 |
| AA200-pKP4 | 2/20 | 16/20 |
| AA200-sc | 0/5 | 0/5 |

Example 2

Conversion of D-glucose to 1,3-propanediol by E. coli Strain AA200, Transformed with Klebsiellia pneumoniae DNA Containing Dehydratase Activity Glass serum bottles, filled to capacity with media (ca. 14 mL of Medium A as defined in Example 1 supplemented with 10 μg/mL kanamycin and 0.2% D-glucose, plus or minus 0.5-1.0 mM cyclic adenosine 2':3'-monophosphate (cAMP)), were innoculated with selected single colony isolates of E. coli strain AA200 containing the K. pneumoniae dha regulon cosmids pKP1 or pKP2, the K. pneumoniae pdu operon pKP4, or the Supercos vector alone. In order to avoid contact with glycerol, the innoculation was performed from either an agar plate of LB-50amp or from a liquid culture of the same medium. The reactions were incubated for ca. 72 hr at 30° C. while shaking at 250 rpm. Growth was determined by the change in absorbance at 600 nm where the initial OD$_{600}$ was 0.020 AU. The extent of glucose depletion and product distribution were determined by HPLC. Single colony isolates are identified by a numbered suffix "-x", e.g., AA200-pKP1-x. Cumulative results are presented in Table 3 and Table 4.

TABLE 3

Conversion of 0.2% D-glucose to 1,3-propanediol by transformed E. coli strain AA200: without cAMP

| Transformant | OD$_{600}$ | [1,3-propanediol] (mM) | Con. (%) | Sel. (%) |
|---|---|---|---|---|
| AA200-pKP1-3 | 0.056 | 0.05 | 17 | 1 |
| AA200-pKP1-5 | 0.115 | nd | 0 | |
| " | 0.007 | nd | 0 | |
| " | 0.076 | 0.2 | 14 | 5 |
| AA200-pKP1-20 | 0.116 | nd | 27 | 0 |
| " | 0.205 | 0.3 | 17 | 8 |
| AA200-pKP2-10 | 0.098 | 0.2 | 13 | 7 |
| AA200-pKP2-14 | 0.117 | 0.5 | 17 | 14 |
| " | 0.129 | 0.2 | 19 | 5 |
| AA200-pKP2-20 | 0.094 | nd | 11 | 0 |
| AA200-pKP4-4 | 0.198 | 0.1 | 28 | 2 |
| AA200-pKP4-19 | 0.197 | 0.2 | 34 | 3 |
| AA200-pKP4-20 | 0.206 | 0.1 | 38 | 1 |
| AA200-sc-1 | 0.097 | nd | 22 | 0 |
| " | 0.176 | nd | 46 | 0 |

TABLE 4

Conversion of 0.2% D-glucose to 1,3-propanediol by transformed E. coli strain AA200: with cAMP

| Transformant | OD$_{600}$ | [1,3-propanediol] (mM) | % Con. | % Sel. |
|---|---|---|---|---|
| AA200-pKP1-3 | 0.102 | 0.5 | 19 | 12 |
| AA200-pKP1-5 | 0.088 | 1.5 | 21 | 37 |
| " | 0.236 | 1.4 | 24 | 28 |
| " | 0.071 | 0.8 | 15 | 23 |
| AA200-pKP1-20 | 0.153 | nd | 40 | 0 |
| " | 0.185 | 0.9 | 27 | 16 |
| AA200-pKP2-10 | 0.098 | 0.2 | 13 | 7 |
| AA200-pKP2-14 | 0.213 | 2.0 | 26 | 27 |
| " | 0.155 | 0.6 | 25 | 12 |
| AA200-pKP2-20 | 0.198 | 1.2 | 40 | 14 |
| AA200-pKP4-4 | 0.218 | 0.1 | 31 | 2 |
| AA200-pKP4-19 | 0.223 | 0.2 | 37 | 3 |
| AA200-pKP4-20 | 0.221 | 0.2 | 35 | 3 |
| AA200-sc-1 | 0.111 | nd | 23 | 0 |

TABLE 4-continued

Conversion of 0.2% D-glucose to
1,3-propanediol by transformed
E. coli strain AA200: with cAMP

| Transformant | OD$_{600}$ | [1,3-propanediol] (mM) | % Con. | % Sel. |
|---|---|---|---|---|
| " | 0.199 | nd | 49 | 0 |
| " | 0.122 | nd | 25 | 0 |

$^a$The identity of 1,3-propanediol was verified by GC/MS as described in the GENERAL METHODS.

Example 3

Conversion of D-glucose to 1,3-propanediol by *E. coli* Strain DH5α, Transformed with *Klebsiella pneumoniae* DNA Containing Dehydratase Activity

*E. coli* strain DH5α, containing the *K. pneumoniae* dha regulon cosmids pKP1 or pKP2, were tested for their ability to convert D-glucose to 1,3-propanediol as described in Example 2. The results are presented in Table 5.

TABLE 5

Conversion of 0.2% D-glucose to 1,3-propanediol
by transformed E. coli strain DH5α:
plus (+) and minus (−) cAMP

| Transformant | OD$_{600}$ | [1,3-propanediol] (mM) | % Con. | % Sel. |
|---|---|---|---|---|
| DH5α-pKP1 (−) | 0.630 | 0.5 | 100 | 2 |
| DH5α-pKP1 (+) | 0.774 | 0.6 | 100 | 3 |
| DH5α-pKP2 (−) | 0.584 | 0.6 | 100 | 3 |
| DH5α-pKP2 (+) | 0.699 | 0.7 | 100 | 3 |

Example 4

Conversion of D-glucose to 1,3-propanediol by *E. coli* Strain ECL707 Transformed with *Klebsiella pneumoniae* DNA Containing Dehydratase Activity

*E. coli* strain ECL707, containing the *K. pneumoniae* dha regulon cosmids pKP1 or pKP2, the *K. pneumoniae* pdu operon pKP4, or the Supercos vector alone, were tested for their ability to convert D-glucose to 1,3-propanediol as described in Example 2. In each case, conversion was quantitative. The results are presented in Table 6.

TABLE 6

Conversion of D-glucose to 1,3-propanediol
by transformed E. coli strain ECL707:
with and without cAMP

| Transformant | OD$_{600}$ (without cAMP) | [1,3-propanediol] (mM) (without cAMP) | OD$_{600}$ (with cAMP) | [1,3-propanediol] (mM) (with cAMP) |
|---|---|---|---|---|
| ECL707-pKP1-1 | 0.607 | 0.1 | 0.475 | 0.1 |
| ECL707-pKP1-3 | 0.619 | 0.1 | 0.422 | 0.1 |
| ECL707-pKP1-7 | 0.582 | 0.2 | 0.522 | 0.2 |
| ECL707-pKP1-10 | 0.593 | 0.1 | 0.408 | 0.1 |
| ECL707-pKP1-18 | 0.584 | 0.1 | 0.433 | 0.1 |
| ECL707-pKP2-4 | 0.588 | 0.1 | 0.408 | 0.1 |
| ECL707-pKP2-5 | 0.630 | 0.1 | 0.516 | 0.2 |

TABLE 6-continued

Conversion of D-glucose to 1,3-propanediol
by transformed E. coli strain ECL707:
with and without cAMP

| Transformant | OD$_{600}$ (without cAMP) | [1,3-propanediol] (mM) (without cAMP) | OD$_{600}$ (with cAMP) | [1,3-propanediol] (mM) (with cAMP) |
|---|---|---|---|---|
| ECL707-pKP2-8 | 0.542 | 0.1 | 0.486 | 0.1 |
| ECL707-pKP2-15 | 0.589 | 0.1 | 0.485 | 0.1 |
| ECL707-pKP2-19 | 0.577 | 0.1 | 0.504 | 0.1 |
| ECL707-pKP4-8 | 0.499 | nd | 0.361 | <0.1 |
| ECL707-pKP4-9 | 0.544 | nd | 0.354 | nd |
| ECL707-pKP4-10 | 0.515 | nd | 0.265 | <0.1 |
| ECL707-pKP4-14 | 0.512 | nd | 0.318 | <0.1 |
| ECL707-pKP4-17 | 0.545 | nd | 0.388 | <0.1 |
| ECL707-sc-1 | 0.592 | nd | 0.385 | nd |

Example 5

Two Stage Conversion of D-glucose to
1,3-propanediol by *Escherichia coli* AA200-pKP1-5

Baffled flasks (250 mL) containing 50 mL LB-amp medium were inoculated with single colonies of AA200-pKP1-5. The cells were grown, in duplicate, overnight at 30 or 37° C. with shaking (250 rpm).

Grown cultures were spun (10 minutes, 10,000 rpm, 4° C.) and resuspended in production medium without glucose (10 mM (NH$_4$)$_2$SO$_4$; 5 mM potassium phosphate buffer, pH 7.5; 50 mM MOPS, pH 7.5; 0.01% yeast extract; 0.01% casamino acids; 0.8 μg/mL vitamin B$_{12}$; and 50 μg/mL ampicillin) containing either trace metals A: (0.08 μM CoCl$_2$, 0.06 μM CuCl$_2$, 7 μM FeSO$_4$, 2 μM H$_3$BO$_4$, 0.2 μM MnCl$_2$, 0.1 μM Na$_2$MoO$_4$, 0.08 μM NiCl$_2$, 0.3 μM ZnSO$_4$, and 0.03 mM thiamine) or trace metals B: (0.7 mM CaCl$_2$, 2.53 μM CoCl$_2$, 1.72 μM CuSO$_4$, 1.0 μM FeCl$_3$, 2 mM MgCl$_2$, 0.05 mM MnCl$_2$, 2.42 μM Na$_2$MoO$_4$, 1.0 μM ZnCl$_2$, and 0.03 mM thiamine). The cells were spun a second time, resuspended in 50 mL fresh production medium containing D-glucose and dispensed into 60 mL serum bottles which were capped and sealed with butyl rubber septa The bottles were shaken (250 rpm) and samples withdrawn with a syringe through the septum and filtered through a 0.2 μfilter before analysis. Results are shown in Table 7 and Table 8; residual glucose was measured by enzymatic analysis (Biochemistry Analyzer, Yellow Springs Instruments Co., Inc.) and 1,3-prop anediol was analyzed by HPLC.

TABLE 7

Conversion of 0.2% D-glucose to 1,3-propanediol by
Escherichia coli AA200-pKP1-5.
Duplicate reactions were performed$^a$

| Experiment | Time (days) | [Glucose] (mM) | [1,3-propanediol] (mM) | Con. (%) | Sel. (%) |
|---|---|---|---|---|---|
| #1 | 1 | 0.1 | 2.3 | 99 | 10 |
| #1 | 4 | 0.1 | 2.3 | 99 | 10 |
| #2 | 1 | 2.8 | 2.3 | 75 | 14 |
| #2 | 4 | 0.1 | 2.4 | 99 | 11 |

$^a$The reactions mixtures, containing trace metals A, were incubated at 37° C.

TABLE 8

Conversion of 1% D-glucose to
1,3-propanediol by *Escherichia coli* AA200-kP1-5[a]

| time (days) | [glucose] (mM) | [1,3-propanediol] (mM) | Con. (%) | Sel. (%) |
|---|---|---|---|---|
| 0 | 53 | 0 | 0 | 0 |
| 1 | 39 | 5.6 | 26 | 20 |
| 2 | 35 | 8.3 | 34 | 23 |
| 3 | 33 | 8.4 | 38 | 21[b] |

[a] The reactions mixtures, containing trace metals B, were incubated at 30° C.
[b] At the end of the reaction, the presence of 1,3-propanediol was confirmed by GC/MS and $^{13}$C-NMR (300 MHz).

Example 6

Conversion of D-glucose to 1,3-propanediol by *Klebsiella pneumoniae* ECL2106 but not by *Klebsiella pneumoniae* ATCC 25955

Glass serum bottles, filled to capacity (ca 14 mL) with media, were lightly innoculated from a LB agar plate containing *K. pneumoniae* ECL2106 or *K. pneumoniae* ATCC 25955. The media contained 50 mM glucose, 3 mM $(NH_4)_2SO_4$, 0.9 mM $CaCl_2$, 4 µM $CoCl_2$, 0.06 µM $CuCl_2$, 7 µM $FeSO_4$, 2 µM $H_3BO_4$, 0.8 mM $MgSO_4$, 0.2 µM $MnCl_2$, 0.1 µM $Na_2MoO_4$, 0.08 µM $NiCl_2$, 0.3 µM $ZnSO_4$, 0.1 mg/mL DL-cysteine, 10 µM ethylenediaminetetraacetic acid, 0.8 µg/mL vitamin $B_{12}$, potassium phosphate as indicated in Table 9, and either 50 mM HEPES or 50 mM MOPS buffer, pH 7.5. The reactions were incubated for 47 hr at 30° C. while shaking at 250 rpm. Otherwise, the reaction was performed as described in Example 2. The results are given in Table 9.

TABLE 9

Conversion of D-glucose to 1,3-propanediol by *Klebsiella pneumoniae* ECL2106 but not by *Klebsiella pneumoniae* ATCC 25955

| Strain | Buffer | Pi (mM) | [Glucose] (mM) | [1,3-Propanediol] (mM) |
|---|---|---|---|---|
| 2106 | MOPS | 5.0 | 11.4 | 0.2 |
| 2106 | MOPS | 2.5 | 13.9 | 0.2 |
| 2106 | MOPS | 1.3 | 14.8 | 0.1 |
| 2106 | MOPS | 0.6 | 15.8 | 0.1 |
| 2106 | HEPES | 5.0 | 21.1 | 0.1 |
| 2106 | HEPES | 2.5 | 23.4 | 0.1 |
| 2106 | HEPES | 1.3 | 26.4 | 0.1 |
| 2106 | HEPES | 0.6 | 27.5 | 0.1 |
| 25955 | MOPS | 5.0 | 4.4 | nd |
| 25955 | MOPS | 2.5 | 5.4 | nd |
| 25955 | MOPS | 1.3 | 2.8 | nd |
| 25955 | MOPS | 0.6 | 7.8 | nd |
| 25955 | HEPES | 5.0 | 7.0 | nd |
| 25955 | HEPES | 2.5 | 13.5 | nd |
| 25955 | HEPES | 1.3 | 10.2 | nd |
| 25955 | HEPES | 0.6 | 17.8 | nd |

Example 7

Production of 1,3-propanediol by Recombinant *Pichia pastoris* Construction of General Purpose Expression Plasmid The 0.9 kb EcoRI/XbaI fragment in pHIL-D4 (Phillips Petroleum, Barlesville, Okla.) was replaced by the 0.9 kb EcoRI/XbaI fragment from pAO815 (Invitrogen, San Diego, Calif.) to generate the plasmid pHIL-D4B2 which contains the following elements: 5'AOX1, *P. pastoris* methanol inducible alcohol oxidase I (AOX1) promoter; AOX1 term, *P. pastoris* AOX I transcriptional termination region; HIS4, *P. pastoris* histidinol dehydrogenase-encoding gene for selection in his4 hosts; kan, sequence derived from transposon Tn903 encoding aminoglycoside 3'-phosphotransferase, conferring kanamycin, neomycin and G418 resistance in a wide variety of hosts, and useful as an indicator of cassette copy number; 3'AOX1, *P. pastoris* sequence downstream from AOX1, used in conjunction with 5'AOX1 for site-directed vector integration; ori, pBR322 origin of DNA replication allowing plasmid manipulations in *E. coli*; and amp, β-lactamase gene from pBR322 conferring resistance to ampicillin. An additional feature of pHIL-D4B2 is that multiple expression cassettes (5'AOX1—gene—AOX1 term) can easily be placed onto one plasmid by subcloning cassettes on Bgl2/XbaI fragments into BamH1/XbaI sites.

Construction of Plasmid for Co-Expression of dhaB1 and dhaB2

The open reading frames for dhaB1 and dhaB2 were amplified from cosmid pKP1 by PCR using primers (SEQ ID NO:2 with SEQ ID NO:3 and SEQ ID NO:4 with SEQ ID NO:5 for dhaB1 and dhaB2, respectively) incorporating EcoR1 sites at the 5' ends (10 mM Tris pH 8.3, 50 mM KCl, 1.5 mM $MgCl_2$, 0.0001% gelatin, 200 µM dATP, 200 µM dCTP, 200 µM dGTP, 200 µM dTTP, 1 µM each primer, 1-10 ng target DNA, 25 units/mL Amplitaq® DNA polymerase Perkin Elmer Cetus, Norwalk Conn.). PCR parameters were 1 min at 94° C., 1 min at 55° C., 1 min at 72° C., 35 cycles. The products were subcloned into the EcoR1 site of pHIL-D4B2 to generate the expression plasmids pMP19 and pMP20 containing dhaB1 and dhaB2, respectively.

The dhaB1 expression cassette on a Bgl2/Xba1 fragment from pMP19 was subcloned into the BamH1/Xba1 site of pMP20 to generate pMP21. Plasmid pMP21 contains expression cassettes for both dhaB2 and dhaB1, and the HIS4 selectable marker.

Construction of Plasmid for Co-Expression of dhaB3 and dhaT

The open reading frames for dhaT and dhaB3 were amplified by PCR from cosmid pKP1 using primers (SEQ ID NO:6 with SEQ ID NO:7 and SEQ ID NO:8 with SEQ ID NO:9 for dhaT and dhaB3, respectively) incorporating EcoRI sites at the 5' ends. The products were subcloned into the EcoRI site of pHIL-D4B2 to generate the expression plasmids pMP17 and pMP18 containing dhaT and dhaB3, respectively.

The dhaT expression cassette on a Bgl2/Xba1 fragment from pMP17 was subcloned into the BamHI/Xba1 site of pMP18 to generate pMP22 which contains expression cassettes for both dhaT and dhaB3.

The 4.1 kb EcoR1 fragment containing SUC2 was deleted from pRK20 (Phillips Petroleum, Bartlesville, Okla.) to generate pMP2. SUC2 encodes for an invertase which may be used a second selectable marker in *Pichia*. The 4.0 kb Hind3 fragment containing lacZ was deleted form pMP2 to generate pMP3. The 0.4 kb Hind3 fragment containing AOX1 term from pHIL-D4 was subcloned into the Hind3 site of pMP3 to generate pMP10.

The 2.0 kb Bgl2/Xba1 fragment in pMP10 was replaced with the 5.0 kb Bgl2/Xba1 fragment containing the dhaB3 and dhaT expression cassettes from pMP22 to generate pMP23. The 5.4 kb PstI/Bgl2 fragment containing SUC2 from pRK20 was subcloned into the PstI/Bgl2 sites of pSP73 (Promega, Madison, Wis.) to generate pMP11a. Plasmid pMP11a was cut with EcoR1, filled with T4 DNA polymerase and religated to generate pMP11b. The 1.1 kb Pst/Bgl2 fragment in pMP10 was replaced with the 5.4 kb Bgl2/PstI fragment containing SUC2 from pMP11b to generate pMP12.

The 1.0 kb Sca1/Bgl2 fragment in pMP23 was replaced with the 5.2 kb Sca1/Bgl2 fragment containing SUC2 from pMP12 to generate pMP24. Plasmid pMP24 contains expression cassettes for both dhaT and dhaB3, and the SUC2 selectable marker.

Transformation of *P. pastoris* with dhaB1/dhaB2 Expression Plasmid pMP21

*P. pastoris* strain GTS 115(his4) (Phillips Petroleum, Bartlesville, Okla.) was transformed with 1-2 ug of Bgl2-linearized plasmid pMP21 using the spheroplast transformation method described by Cregg et al., (*Mol. Cell. Biol.* 5, 3376, (1985)). Cells were regenerated on plates without histidine for 3-4 days at 30° C. All transformants arise after integration of plasmid DNA into the chromosome. Transformants were patched onto a YPD (1% Bacto yeast extract, 2% peptone, 2% glucose) master plate.

Screening of *P. pastoris* Transformants for dhaB1 and dhaB2

Chromosomal DNA was prepared from his⁺ transformants described above and subjected to PCR analysis with primers specific for dhaB1 and dhaB2. High copy number strains were selected from transformants containing both dhaB1 and dhaB2 by growth in YPD media supplemented with increasing levels of G418 (Sigma, St. Louis, Mo.) up to 2000 μg/mL. Resistance to a high level of G418 suggests significant duplication of expression cassettes.

Secondary Transformation of *P. pastoris* with dhaB3/dhaT Expression Plasmid pMP24

Transformants with resistance to a high level of G418 as described above were re-transformed with plasmid pMP24 using the spheroplast transformation method. Cells were first regenerated on non-selective plates for 2 days at 30° C., after which top agar containing the regenerated cells was scraped from the plate and vortexed extensively in 20 mL water. After passing through 4 folds of cheesecloth, the cells were pelleted by centrifugation and resuspended in 10 mL water. Aliquots of 200 uL were plated onto sucrose plates, and incubated for 2 days at 30° C. All transformants arise after integration of plasmid DNA into the chromosome. Transformants appear as large colonies in a background of small colonies, and require isolation. After 24 h growth with shaking at 30° C. in Msu media (per L, 13.4 g yeast nitrogen base w/o amino acids, 10 g sucrose, 0.4 g biotin), transformants were streaked onto Msu plates (Msu media plus 15 g/L agar) and grown for 2 days at 30° C. Large isolated colonies were patched onto a YPD master plate.

Screening of *P. pastoris* Double Transformants for dhaB1, dhaB2, dhaB3, and dhaT and Their Corresponding Enzyme Activities Chromosomal DNA was prepared from suc⁺ double transformants described above and subjected to PCR analysis with primers specific for dhaB1, dhaB2, dhaB3, and dhaT. Thus, the presence of all four open reading frames was confirmed.

The presence of active glycerol dehydratase (dhaB) and 1,3-propanediol oxido-reductase (dhay) was demonstrated using in vitro enzyme assays. Additionally, western blot analysis confirmed protein expression from all four open reading frames. Cell free extracts for these protein characterizations were prepared as follows. Double transformants containing dhaB1, dhaB2, dhaB3, and dhaT were grown aerobically with shaking at 30° C. in MGY (Per L, 13.4 g yeast nitrogen base w/o amino acids, 0.4 mg biotin, 10 mL glycerol) for 2 days. The cells were pelleted by centrifugation, resuspended in MM (Per L, 13.4 g yeast nitrogen base w/o amino acids, 0.4 mg biotin, 5 mL methanol) and incubated as above. After approximately 24 h, the cells were harvested, resuspended in buffer (0.1 M tricene/KOH buffer, pH 8.2, 50 mM KCl, and 2% 1,2-propanediol), mechanically disrupted (using a glass rod while vortexing in the presence of glass beads), and centrifuged.

One strain that showed positive for the presence of all four open reading frames (dhaB1, dhaB2, dhaB3, and dhaT) and their corresponding activities was designated MSP42.81 and was selected for further study.

In Vivo Production of 1,3-propanediol Using Recombinant *Pichia pastoris*

*P. pastoris* MSP42.81 (ATCC 74363) were grown in a BiostatB fermenter (B Braun Biotech, Inc.) in 1.5 L minimal medium containing 8.5 g/L $KH_2PO_4$, 2.1 g/L $(NH_4)_2SO_4$, 10 g/L glycerol, 2.3 g/L $MgSO_4 7H_2O$, 0.18 g/L $CaSO_4 2H_2O$, and 0.29 mL/L PTMI. PTMI is a stock mineral solution containing 24 mM $CuSO_4$, 4.8 mM KI, 18 mM $MnSO_4$, 0.8 mM $Na_2MoO_4$, 0.3 mM $H_3BO_3$, 2.1 mM $CoCl_2$, 70 mM $ZnSO_4$, 26 mM $H_2SO_4$, 234 mM $FeSO_4$, and 0.8 mM biotin. The fermenter was controlled at pH 5.0 with addition of 2 M $NH_4OH$, 30° C., and 30% dissolved oxygen tension through agitation control. A culture of *P. pastoris* MSP42.81 grown in YM broth at 30° C. was used as an inoculum; 20 mL of the culture was used to inoculate the fermenter.

When glycerol was shown to be depleted (24 h after inoculation), induction of the AOX promoters was initiated by the addition of a methanol feed. The feed contained 1 liter of methanol, 5 mL PTMI and 5 mL of a stock biotin solution prepared as 0.2 g/L in water. The methanol solution was added manually to maintain an average concentration of 0.5% as determined by HPLC analysis. Fifty mL of cells $OD_{600}=20$ AU) were removed from the reactor after 15 h of induction.

The 50 mL cell suspension was pelleted and resuspended in 12.5 mL nitrogen sparged base medium (6.7 g/L yeast nitrogen base, 3.0 g/L yeast extract, 1.0 g/L $K_2HPO_4$, 1.0 g/L $KH_2PO_4$, 3.0 g/L $(NH_4)_2SO_4$, titrated to pH 7.2 and filter sterilized). Coenzyme $B_{12}$, prepared as a stock solution at 2 mg/mL in nitrogen sparged water, was added to the cell suspension to give a final concentration of 20 μg/mL. Three media stock solutions were prepared in base medium containing 1% glucose, 0.5% glucose and 0.5% glycerol (w/v), and 1.0% glycerol (w/v). A stock solution of chloroquine (1.06 g/50 mL, pH 7.2) was also prepared.

Two mL of the media stock solutions and 1 mL mixtures of chloroquine and water to give the final concentrations listed in Table 10 were placed in 10 mL crimp sealed serum bottles and sparged with nitrogen before adding 1 mL of cells with coenzyme $B_{12}$ mixture. The serum bottles were incubated at 30° C. with shaking. Samples taken immediately after the addition of cells and after 24 h incubation were analyzed by HPLC. The results are shown in Table 10.

TABLE 10

In vivo production of 1,3-propanediol using recombinant Pichia pastoris

| reaction | medium[a] | chloroquine (mM) | 1,3-propanediol (mM) |
|---|---|---|---|
| 1 | glu[b] | 0 | 0.04 |
| 2 | glu | 2.5 | 0.2 |
| 3 | glu | 5.0 | 0.1 |
| 4 | glu | 10.0 | 0.1 |
| 5 | glu[b]/gly | 0 | 0.2 |
| 6 | glu/gly | 2.5 | 0.4 |

TABLE 10-continued

In vivo production of 1,3-propanediol
using recombinant Pichia pastoris

| reaction | medium[a] | chloroquine (mM) | 1,3-propanediol (mM) |
|---|---|---|---|
| 7 | glu/gly | 5.0 | 0.4 |
| 8 | glu/gly | 10.0 | 1.2[c] |
| 9 | gly | 0 | 0.2 |
| 10 | gly | 2.5 | 0.3 |
| 11 | gly | 5.0 | 0.3 |
| 12 | gly | 10.0 | 1.4[c] |

[a]Less than 10% of each substrate was used in 24 h unless noted.
[b]No glucose remained after 24 h.
[c]The presence of 1,3-propanediol was confimed by GC/MS as described in GENERAL METHODS.

Example 8

Use of a *Pichia pastoris* Double Transformant for Production of 1,3-propanediol from D-Glucose

*P. pastoris* MSP42.81 were grown in a BiostatB fermenter (B Braun Biotech, Inc.) in 1.5 L minimal medium containing 8.5 g/L $KH_2PO_4$, 2.1 g/L $(NH_4)_2SO_4$, 10 g/L glucose, 2.3 g/L $MgSO_4 7H_2O$, 0.18 g/L $CaSO_4 2H_2O$, and 0.29 mL/L PTMI. Otherwise, fermentation and induction conditions were identical to those described in Example 7. Fifty mL of cells were removed from the reactor after 15 h of induction.

The cell suspension was handled as described in Example 7, with the exception that a modified base medium (6.7 g/L yeast nitrogen base, 1.0 g/L $KH_2PO_4$, 1 g/L $K_2HPO_4$, 3 g/L $(NH_4)_2SO_4$, titrated to pH 7.2 and filter sterilized) was used. The three media stock solutions were prepared in this modified base medium as well. All other solutions were the same. Reaction mixtures were prepared as described, and incubated at 30° C. with shaking. Samples taken immediately after the addition of cells and after 75 hours incubation were analyzed by HTLC. In a reaction containing glucose as the carbon source and 5 mM chloroquine, 0.17 mM 1,3-propanediol was produced.

Example 9

Plasmid Construction for the Transformation and Expression of dhaB and dhaT in *Saccharomyces cerevisiae*

Construction of General Purpose Expression Plasmids

Two types of expression plasmids were created, those that could integrate by recombination into chromosomes, and those that could exist as replicating episomal elements. For each type of general expression plasmid a yeast promoter was present and separated from a yeast transcription terminator by fragments of DNA containing recognition sites for one or more restriction endonucleases. Each type of general expression plasmid also contained the gene for β-lactamase for selection in *E. coli* on media containing ampicillin, an origin of replication for plasmid maintainence in *E. coli*, and either a 2 micron origin of replication for episomal elements or sequences homologous to those found in *S. cerevisiae* chromosomes for recombination and integration of introduced DNA into chromosomes. The selectable nutritional markers used for yeast and present on the expression plasmids were one of the following: HIS3 gene encoding imidazoleglycerolphosphate dehydratase, URA3 gene encoding orotidine 5'-phosphate decarboxylase, TRP1 gene encoding N-(5'-phosphoribosyl)-anthralate isomerase and LEU2 encoding β-isopropylmalate dehydrogenase. The yeast promoters used were ADH1 or GAL1, and the transcription terminators ADH1, CYC1 or AOX1; the latter from *Pichia pastoris*.

Plasmid pGADGH (Clontech, Palo Alto, Calif.) was digested with HindIII and the single-strand ends converted to EcoRI ends by ligation with HindIII-XmnI and EcoRI-XmnI adaptors (New England Biolabs, Beverly, Mass.). Selection for plasmids with correct EcoRI ends was achieved by ligation to a kanamycin resistance gene on an EcoRI fragment from plasmid pUC4K (Pharmacia Biotech, Uppsala), transformation into *E. coli* strain DH5α and selection on LB plates containing 25 μg/mL kanamycin. The resulting plasmid (pGAD/KAN2) was digested with SnaBI and EcoRI and a 1.8 kb fragment with the ADH1 promoter was isolated. Plasmid pGBT9 (Clontech, Palo Alto, Calif.) was digested with SnaBI and EcoRI, and the 1.5 kb ADH1/GAL4 fragment replaced by the 1.8 kb ADH1 promoter fragment isolated from pGAD/KAN2 by digestion with SnaBI and EcoRI. The resulting vector (PMCK11) is a replicating plasmid in yeast with ADH1 promoter and terminator and a TRP1 marker.

Plasmid pGADGH was digested with SnaBI and HindIII and a 1.8 kb fragment containing the ADH1 promoter isolated. This fragment was ligated into the vector pRS405 (Stratagene, La Jolla, Calif.) previously digested with SmaI and HindIII. Positive clones were identified by insertional-inactivation of the plasmid-encoded lacZ alpha peptide and the presence of the ADH1 promoter fragment. The resulting plasmid (pMCK4) contained an ADH1 promoter and a LEU2 marker.

The ~0.2 kb NaeI-EcoRI fragment from pGBT9 containing the ADH1 terminator was ligated to EcoRI-HindIII digested pRS403 (Stratagene, La Jolla, Calif.) to yield the ~4.8 kb plasmid pRVN5. The ~2.0 kb SnaBI-EcoRI fragment from pGAD/KAN2 containing the ADH1 promoter was ligated to SmaI-EcoRI digested pRVN5 to yield the ~6.8 kb plasmid pRVN6 with the ADH1 promoter and terminator and a unique EcoRI cloning site in between.

The 0.4 kb HindIII fragment from pGADGH containing an additional XmnI site was deleted and the vector was religated to yield the 7.0 kb vector pGAD-D3. Vector pGAD-D3 was digested with XmnI and the ~2.4 kb fragment containing the ADH1 promoter and terminator and an intervening HindIII cloning site was purified. The pRS404 vector (Stratagene, La Jolla, Calif.) was digested with PvuII and the larger 3.8 kb fragment with TRP1 was purified and ligated to the XmnI promoter and terminator fragment from pGAD-D3 to give plasmid pRVN11.

The open reading frames for dhaT, dhaB3, and dhaB1 were amplified from pHK28-26 (SEQ ID NO:1) by PCR using primers (SEQ ID NO:6 with SEQ ID NO:7, SEQ ID NO:8 with SEQ ID NO:9, and SEQ ID NO:2 with SEQ ID NO:3 for dhaT, dhaB3, and dhaB1, respectively) incorporating EcoR1 sites at the 5' ends (10 mM Tris pH 8.3, 50 mM KCl, 1.5 mM $MgCl_2$, 0.0001% gelatin, 200 μM dATP, 200 μM dCTP, 200 μM dGTP, 200 μM dTTP, 1 μM each primer, 1-10 ng target DNA, 25 units/mL Amplitaq® DNA polymerase (Perkin Elmer Cetus, Norwalk Conn.)). PCR parameters were 1 min at 94° C., 1 min at 55° C., 1 min at 72° C., 35 cycles. The products were subcloned into the EcoR1 site of pHIL-D4 (Phillips Petroleum, Bartlesville, Okla.) to generate the plasmids pMP13, pMP14, and pMP15 containing dhaT, dhaB3, and dhaB1, respectively.

Construction of Plasmids for Expression of dhaT

The replicating plasmid pGAD/KAN2 was digested with EcoRI to remove the kanamycin resistance fragment, dephosphorylated, and ligated to the dhaT EcoRI fragment from pMP13. The resulting plasmid (pMCK13) had dhaT correctly oriented for transcription from the ADH1 promoter and contained a LEU2 marker.

Plasmid pRNV6 was digested with EcoRI and ligated to the dhaT EcoRI fragment from pMP13. The resulting plasmid (pRVN6T) had dhaT correctly orientated for transcription from the ADH1 promoter and contained a HIS3 marker.

Construction of Plasmids for Expression of dhaB1

The replicating plasmid pGADGH was digested with HindIII, dephosphorylated, and ligated to the dhaB1 HindIII fragment from pMP15. The resulting plasmid (pMCK10) had dhaB1 correctly oriented for transcription from the ADH1 promoter and contained a LEU2 marker.

Construction of Plasmids for Expression of dhaB2

The replicating plasmid pMCK11 was digested with EcoRI, dephosphorylated, and ligated to the dhaB2 EcoRI fragment from pMP20. The resulting plasmid (pMCK17) had dhaB2 correctly oriented for transcription from the ADH1 promoter and contained a TRP1 marker.

Plasmid pRS403 was digested with SmaI and ligated to a SnaBI/NaeI dhaB2 fragment from pMCK17. The resulting plasmid pMCK21) had dhaB2 correctly orientated for transcription from the ADH1 promoter and contained a HIS3 marker.

Construction of Plasmids for Expression of dhaB3

The replicating plasmid pYES2 (Invitrogen, San Diego, Calif.) was digested with EcoRI, dephosphorylated, and ligated to the dhaB3 EcoRI fragment from pMP14. The resulting plasmid (pMCK1) had dhaB3 correctly oriented for transcription from the GAL1 promoter and contained a URA3 marker.

The replicating plasmid pGAD/KAN2 was digested with EcoRI, dephosphorylated, and ligated to the dhaB3 EcoRI fragment from pMP14. The resulting plasmid (pMCK15) had dhaB3 correctly oriented for transcription from the ADH1 promoter and contained a LEU2 marker.

Plasmid pRS404 was digested with Pst and HincII and ligated to the PstI/EcoRV dhaB3 fragment from pMCK15. The resulting plasmid (pMCK20) had dhaB3 correctly orientated for transcription from the ADH1 promoter and contained a TRP1 marker.

Transformation of S. cerevisiae with dha Expression Plasmids

S. cerevisiae strain YPH499 (ura3-52 lys2-801 ade2-101 trp1-del63 his3-del200 leu2-dell) (Stratagene, La Jolla, Calif.) was transformed with 1-2 µg of plasmid DNA using a LiCl/polyethylene glycol protocol published by Stratagene (Catalog #217406). Alternatively, transformation was achieved using a Frozen-EZ Yeast Transformation Kit (Catalog #T2001) from Zyrno Research (Orange, Calif.). Colonies were grown on Supplemented Minimal Medium (SMM–0.67% yeast nitrogen base without amino acids, 2% glucose) for 3-4 days at 29° C. with one or more of the following additions: adenine sulfate (20 mg/L), uracil (20 mg/L), L-tryptophan (20 mg/L), L-histidine (20 mg/L), L-leucine (30 mg/L), L-lysine (30 mg/L). Colonies were streaked on selective plates and used to inoculate liquid media. Depending on the vector used, colonies arose either after integration of plasmid DNA or from replication of an episome. In addition to transformations with single plasmid types, co-transformations with two or more plasmids were carried out.

Expression of dhaB Activity in Transformed S. cerevisiae

Strain YPH499 transformed with plasmids pMCK1, pMCK10 and pMCK17 was grown on Supplemented Minimal Medium containing 0.67% yeast nitrogen base without amino acids, 2% galactose, 2% raffinose, 20 mg/L adenine sulfate, 30 mg/L L-lysine and 20 mg/L histidine. Cells were homogenized and extracts assayed for dhaB activity. A specific activity of 0.021 units per mg was obtained.

Example 10

Construction of Alternate Replicating and Integration Plasmids for the Transformation of S. cerevisiae A general purpose expression plasmid is constructed by isolating a SnaBI/EcoRI ADH1 promoter fragment from pGAD/KAN2 and ligating this fragment into the vector pRS406 (Stratagene, La Jolla, Calif.) previously digested with HincII and EcoRI. Positive clones are identified by insertional-inactivation of the plasmid-encoded lacZ alpha peptide and the presence of the ADH1 promoter fragment. The resulting plasmid (pMCK3) is digested with EcoRI and SmaI and ligated to the 0.2 kb ADH1 terminator fragment released from plasmid pGBT9 by digestion with EcoRI and NaeI. The resulting plasmid (pMCK5) contains both ADH1 promoter and terminator sequences and a URA3 marker.

Construction of Plasmids for Expression of dhaT

The vector pMCK5 is digested with EcoRI and dephosphorylated. The dhaT gene is excised as an EcoRI fragment from plasmid pMP13 and ligated to pMCK5. The resulting plasmid (pMCK7) has dhaT correctly orientated for transcription from the ADH1 promoter and contains a URA3 marker.

The integration vector pRS404 is digested with KpnI and SacI. The dhaT gene with flanking promoter and terminator is excised as a KpnI/SacI fragment from plasmid pMCK7 and ligated to pRS404. The resulting plasmid has dhaT correctly orientated for transcription from the ADH1 promoter and contains a TRP1 marker.

Construction of Plasmids for Expression of dhaB1

The vector pMCK5 is digested with EcoRI, and dephosphorylated. The dhaB1 gene is excised as an EcoRI fragment from plasmid pMP15 and ligated to pMCK5. The resulting plasmid (pMCK8) has dhaB1 correctly orientated for transcription from the ADH1 promoter and contains a URA3 marker.

The integration vector pRS403 is digested with ClaI and AatII. The dhaB1 gene with flanking promoter and terminator is excised as a ClaI/AatII fragment from plasmid pMCK8 and ligated to pRS403. The resulting plasmid has dhaB1 correctly orientated for transcription from the ADH1 promoter and contains a HIS3 marker.

The replicating plasmid pYES2 is digested with HindIII and SnaBI, and the GAL1 promoter element is replaced by ligation with a SnaBI and HindIII digested ADH1 promoter fragment from pGADGH. A dhaB1 HindIII and XbaI fragment from pMP19 is ligated to those sites in the modified, ADH1 promoter version of pYES2. The resulting plasmid has dhaB1 correctly oriented for transcription from the ADH1 promoter and contains a URA3 marker.

The vector pMCK4 is digested with HindIII and dephosphorylated. The dhaB1 gene is excised as an HindIII fragment from plasmid pMP15 and ligated to pMCK4. The resulting plasmid has dhaB1 correctly orientated for transcription from the ADH1 promoter and contains a LEU2 marker.

Construction of Plasmids for Expression of dhaB2

The vectors pRS404, pRS405 and pRS406 are digested with SmaI. The dhaB2 gene with flanking promoter and terminator is excised as a SnaBI/NaeI fragment from plasmid pMCK17 and ligated to each of the integration vectors. The resulting plasmids have dhaB2 correctly orientated for transcription from the ADH1 promoter and contain either the LEU2, TRP1, or UTRA3 markers.

Example 11

Screenine of *S. cerevisiae* for dha Transformants and Conversion of D-Glucose to 1,3-propanediol Screening of *S. cerevisiae* for dha Genes Chromosomal DNA from Ura+, His+, Trp+ or Leu+ transformants, constructed as described in Examples 9 and 10, is analyzed by PCR using primers specific for each gene, as described for *Pichia pastoris* (SEQ ID NO:2-9).

Production of 1,3-propanediol from D-glucose by *S. cerevisiae* Transformed with dha Genes Transformants containing dhaT, dhaB1, dhaB2 and dhaB3, constructed as described in Examples 9 and 10, are grown aerobically or anaerobically with shaking at 29° C. in SMM supplemented with 20 mg/L adenine sulfate, 30 mg/L L-lysine, 1 mg/L vitamin B12. Growth continues until stationary phase is reached and the presence of 1,3-propanediol is determined by HPLC. Transformant *S. cerevisiae* pMCK1/10/17(HM)#A was deposited and designated ATCC74370.

Example 12

Production of 1,3-propanediol from D-glucose by *Clostridium pasteurianum* ATCC 6013 Under a Hydrogen Atmosphere General Growth Conditions for *Clostridium pasteurianum*

*Clostridium pasteurianum* ATCC 6013 was grown in 60 mL crimp sealed serum bottles containing 10 mL of medium, unless noted. The crimped bottles containing the medium were aseptically sparged with nitrogen prior to innoculation. Basal medium (Medium A), adjusted to pH 7.2, contained the following components in g/L: $KH_2PO_4$, 1.4; $NaH_2PO_4$, 0.69; $NH_4Cl$, 1.8-2.5; KCl, 0.50; $MgSO_4.7H_2O$, 0.50; $CaCl_2$, 0.025; NaCl, 1.0; yeast extract, 2.0; cysteine-HCl, 0.50; sodium bicarbonate, 2.5; p-amino benzoic acid, 0.0080; biotin, 0.000040; sodium citrate-$2H_2O$, 0.10; $FeSO_4.7H_2O$, 0.050; $CoCl_2.6H_2O$, 0.010; $MnCl_2.4H_2O$, 0.0010; $ZnCl_2$, 0.00050; $Na_2MoO_4.2H_2O$, 0.0025; $NiCl_2.6H_2O$, 0.010; and $CUSO_4.5H_2O$, 0.0050; to which carbon components were added as indicated below. All incubations were performed at 30° C. with shaking at 250 rpm.

A 10 mL batch of Medium A supplemented with 5% glucose was inoculated with 1 mL of a frozen stock of *Clostridium pasteurianum* ATCC 6013 which contained approximately 15% (v/v) glycerol, in duplicate. After 96 h, 0.5 mL of the growing cell suspensions was passed into 10 mL of fresh medium and growth was continued. After 24 h, the atmosphere in the newly innoculated vials was pressurized to 30 psi with hydrogen gas and incubation was continued for a further 96 h. The aqueous phase was sampled at the beginning and end of the final 96 h for analysis by BPLC as described in the GENERAL METHODS. The results are shown in Table 11.

TABLE 11

Conversion of D-glucose to 1,3-propanediol by *Clostridium pasteurianum* ATCC 6013 under a hydrogen atmosphere

| Time (h) | Replicate | Glucose (mM) | Glycerol (mM) | 1,3-Propanediol (mM)[a] |
|---|---|---|---|---|
| 0 | A | 114 | nd | 2.7 |
| 96 | A | 47 | nd | 3.4 |
| 0 | B | 119 | 0.1 | 2.0 |
| 96 | B | 59 | 0.1 | 2.5 |

[a]The presence of 1,3-propanediol was confirmed by GC/MS as described in the GENERAL METHODS.

Example 13

Production of 1,3-propanediol from D-glucose be *Clostridium pasteurianum* ATCC 6013 in the Presence of Methyl Viologen Experiment 1. All cells were grown according to the protocol in Example 12. A 10 mL batch of Medium A (described in Example 12) supplemented with 5% glucose was inoculated with 1 mL of a frozen stock of *Clostridium pasteurianum* ATCC 6013 which contained approximately 15% (v/v) glycerol, in duplicate. After 96 h, 0.5 mL of the growing cell suspensions was passed into 10 mL of fresh medium and growth was continued. After 24 h, methyl viologen (1,1'-dimethyl-4,4'-bipyridinium dichloride) was added to the newly innoculated vials to a final concentration of 1 mM and incubation was continued for a further 96 h. The aqueous phase was sampled at the beginning and end of the final 96 h for analysis by HPLC as described in the GENERAL METHODS. The results are shown in Table 12.

TABLE 12

Conversion of D-glucose to 1,3-propanediol by *Clostridium pasteurianum* ATCC 6013 in the presence of methyl viologen

| Time (h) | Replicate | Glucose (mM) | Glycerol (mM) | 1,3-Propanediol (mM)[a] |
|---|---|---|---|---|
| 0 | A | 113 | 0.3 | 2.4 |
| 96 | A | 28 | 1.8 | 3.4 |
| 0 | B | 87 | 0.3 | 2.1 |
| 96 | B | 40 | 3.2 | 4.4 |

[a]The presence of 1,3-propanediol was confirmed by GC/MS as described in the GENERAL METHODS.

Experiment 2. Medium A supplemented with 1% (v/v) glycerol+1% (w/v) glucose was inoculated from a frozen stock of *Clostridium pasteurianum* ATCC 6013, which contained approximately 15% (v/v) glycerol, at a ratio of 0.2 mL frozen stock per 20 mL medium. After 48 h, 10 mL of the cell suspension xwas added to 90 mL of fresh medium and growth was continued for 24 h. The 100 mL cell suspension was chilled on ice and the cells collected by centrifugation under anaerobic conditions. The cells were washed 3× in anaerobic buffer (50 mM phosphate buffer, pH 7.2+0.5 g/L cysteine-HCl, previously gassed with $N_2$ and autoclaved under $N_2$) and resuspended in anaerobic buffer to a volume of 8 mL. In duplicate experiments, one mL of this cell suspension was inoculated into 10 mL of Medium A supplemented with 1% glucose and 0 mM, 1 mM, 5 mM, or 10 mM methyl viologen and incubated for 240 h. The aqueous phase was sampled at the beginning and end of the final 240 h for analysis by HPLC as described in the GENERAL METHODS. The results are shown in Table 13.

TABLE 13

Conversion of D-glucose to 1,3-propanediol by *Clostridium pasteurianum* ATCC 6013 in the presence of methyl viologen (MV)

| MV (mM) | Time (h) | Replicate | Glucose (mM) | Glycerol (mM) | 1,3-Propanediol (mM)[a] |
|---|---|---|---|---|---|
| 0 | 0 | A | 38 | nd | nd |
| " | 240 | A[b] | 40 | nd | nd |
| " | 0 | B | nd | nd | nd |
| " | 240 | B[b] | nd | nd | nd |
| 1 | 0 | A | 40 | nd | nd |
| " | 240 | A[b] | nd | 4 | 1 |
| " | 0 | B | 45 | nd | nd |
| " | 240 | B[b] | nd | 5 | 2 |
| 5 | 0 | A | 37 | nd | nd |
| " | 240 | A | nd | 4 | 2 |
| " | 0 | B | 38 | nd | nd |
| " | 240 | B | nd | 3 | 1 |
| 10 | 0 | A | 40 | nd | nd |
| " | 240 | A | nd | 2 | 5 |
| " | 0 | B | 43 | nd | nd |
| " | 240 | B | nd | 3 | 1 |

[a]The presence of 1,3-propanediol was confirmed by GC/MS as described in the GENERAL METHODS.
[b]By 120 h, glucose was depleted and additional glucose, 1% final concentration, was added.

Experiment 3. *Clostridium pasturanium* ATCC 6013 was initially maintained in thioglycollate medium (Difco®) and transferred to Medium A supplemented with 0.4% glucose for all subsequent studies. After several transfers through the latter medium, an inoculum was prepared by growing a 1 mL aliquot of stock culture in 10 mL the described medium overnight. A series of serum bottles containing methyl viologen at the concentrations indicated in Table 14 in fresh medium bottles were inoculated with 1 mL of the overnight culture and again incubated for the times indicated in Table 14. Bottles were periodically sampled for glucose utilization and analyzed for the presence of 1,3-propanediol and glucose by HPLC as described in the GENERAL METHODS. Table 14 summarizes the analytical results.

TABLE 14

Production of 1,3-propanediol from glucose by *Clostridium pasturanium* ATCC 6013

| bottle | methyl viologen (mM) | time (days) | glucose (mM) | 1,3-propanediol (mM)[a] |
|---|---|---|---|---|
| 1 | 0 | 0 | 22.5 | 0 |
| 1 | 0 | 5 | 0 | 0 |
| 2 | 0.1 | 0 | 26.5 | 0 |
| 2 | 0.1 | 5 | 0 | 0 |
| 3 | 1.0 | 0 | 25.3 | 0 |
| 3 | 1.0 | 5 | 10.0 | 2.4 |
| 3 | 1.0 | 9 | 0 | 2.4 |

[a]The identity of 1,3-propanediol was verified by GC/MS as described in the GENERAL METHODS.

Example 14

Construction of General Purpose Expression Plasmids for Use in Transformation of *Bacillus*, *Streptomyces*, and *Pseudomonas* species The Expression Vector pTacIO The *E. coli* expression vector, pTacIQ contains the lacIq gene (Farabaugh, *Nature* 274, 5673 (1978)) and tac promoter (Amann et al., *Gene* 25, 167 (1983)) inserted into the EcoRI of pBR322 (Sutcliffe et al., *Cold Spring Harb. Symp. Quant. Biol.* 43, 77 (1979)). A multiple cloning site and terminator sequence (SEQ ID NO:10) replaces the pBR322 sequence from EcoRI to SphI.

Subcloning the Glycerol Dehydratase Genes (dhaB1, 2, 3)

The open reading frame for dhaB3 gene was amplified from pHK28-26 by PCR using primers (SEQ D NO:41 and 42), incorporating an EcoRI site at the 5' end and a XbaI site at the 3' end. The product was subcloned into pLitmus29 (New England Biolab, Inc., Beverly, Mass.) to generate the plasmid pDHAB3 containing dhaB3.

The region containing the entire coding region for the four genes of the dhaB operon from pHK28-26 was cloned into pBluescriptII KS+(Stratagene, La Jolla, Calif.) using the restriction enzymes KpnI and EcoRI to create the plasmid pM7.

The dhaBX gene was removed by digesting the plasmid pM7, which contains dhaB(1,2,3,4), with ApaI and XbaI (deleting part of dhaB3 and all of dhaBX). The resulting 5.9 kb fragment was purified and ligated with the 325-bp ApaI-XbaI fragment from plasmid pDHAB3 (restoring the dhaB3 gene) to create pM11, which contains dhaB(1,2,3).

The open reading frame for the dhaB1 gene was amplified from pBY28-26 by PCR using primers (SEQ ID NO:11 and SEQ ID NO:12) incorporating a HindIII site and a consensus RBS ribosome binding site at the 5' end and a XbaI site at the 3' end. The product was subcloned into pLitmus28 (New England Biolab, Inc.) to generate the plasmid pDT1 containing dhaB1.

A NotI-XbaI fragment from pM11 containing part of the dhaB1 gene, the dhaB2 gene and the dhaB3 gene was inserted into pDT1 to create the dhaB expression plasmid, pDT2. The HindIII-XbaI fragment containing the dhaB(1,2,3) genes from pDT2 was inserted into pTacIQ to create pDT3.

Subcloning the 1,3-propanediol Dehydrogenase Gene (dhaT)

The KpnI-SacI fragment of pHK28-26, containing the complete 1,3-propanediol dehydrogenase (dhaT) gene, was subcloned into pBluescriptII KS+ creating plasmid pAH1. The dhaT gene was amplified by PCR from pAH1 as template DNA using synthetic primers (SEQ ID NO:13 with SEQ ID NO:14) incorporating an XbaI site at the 5' end and a BamHI site at the 3' end. The product was subcloned into pCR-Script (Stratagene) at the SrfI site to generate the plasmids pAH4 and pAH5 containing dhaT. The plasmid pAH4 contains the dhaT gene in the correct orientation for expression from the lac promoter in pCR-Script and pAH5 contains the dhaT gene in the opposite orientation. The XbaI-BamHI fragment from pAH4 containing the dhaT gene was inserted into pTacIQ to generate plasmid pAH8. The HindIII-BamHI fragment from pAH8 containing the RBS and dhaT gene was inserted into pBluescriptII KS+ to create pAH11. The HindIII-SalI fragment from pAH8 containing the RBS, dhaT gene and terminator was inserted into pBluescriptII SK+ to create pAH12.

Construction of an Expression Cassette for dhaB(1,2,3) and dhaT

An expression cassette for the dhaB(1,2,3) and dhaT was assembled from the individual dhaB(1,2,3) and dhaT subclones described above using standard molecular biology methods. The SpeI-KpnI fragment from pAH8 containing the RBS, dhaT gene and terminator was inserted into the XbaI-KpnI sites of pDT3 to create pAH23. The SmaI-EcoRI fragment between the dhaB3 and dhaT gene of pAH23 was removed to create pAH26. The SpeI-NotI fragment containing an EcoRI site from pDT2 was used to replace the SpeI-NotI fragment of pAH26 to generate pAH27.

Construction of Expression Cassette for dhaT and dhaB(1,2, 3)

An expression cassette for dhaT and dhaB(1,2,3) was assembled from the individual dhaB(1,Z3) and dhaT subclones described previously using standard molecular biology methods. A SpeI-SacI fragment containing the dhaB(1, 2,3) genes from pDT3 was inserted into pAH11 at the SpeI-SacI sites to create pAH24.

Example 15

Production of 1,3-propanediol by Recombinant *Streptomyces lividans* Subcloning the Glucose Isomerase Promoter Two versions of the glucose isomerase promoter from the vector pCOs121 (SEQ ID NO:15) or pCO121low (SEQ ID NO:16) were amplified by PCR using primers (SEQ ID NO:17 and 18) incorporating SpeI and EcoRI sites at the 5' end and a HindIII site at the 3' end. The products were subcloned into pLitmus29 (New England Biolabs, Inc., Beverly, Mass.) to generate the plasmids pDT7 and pDT8.

Construction of an Expression Cassette for dhaB(1,2,3) and dhaT

The 4.1 kb expression cassette for dhaB(1,2,3) and dhaT from pAH27 (Example 14) was inserted into pDT7 or pDT8 using the restriction enzymes HindIII and SalI to create pDT11 and pDT12, respectively.

Construction of a Plasmid for Co-Expression of dhaB(1,2,3) and dhaT in *Streptomyces*

The 4.3 kb expression cassette for dhaB(1,2,3) and dhaT was removed from pDT11 or pDT12 by digestion with EcoRI and SalI. The vector pU488-101 was digested with the restriction enzymes EcoRI and XbaI. The expression cassette and vector were ligated along with a Sal-Xba Linker (SEQ ID NO:19 and 20) to create pDT13 and pDT14, respectively.

pIJ488-101 consists of replication origin from pIJ101 from *Streptomyces lividans* (Kendall and Cohen, *J. Bacteriol.* 170, 4634 ((1988)) and pUC18 from *E. coli* (Norrander et al., Gene, 26, 101 ((1983)). The sequences are derived as follows: bases 1-2086 are from pIJ101 (1-2086), and bases 7688-8437 are from pIJ101 (8080-8830). Bases 2087-3368 are from the thiostrepton resistance gene from *S. azureus* (Thompson et al., *Gene*, 20, 51 (1982)). Bases 3369-7687 are from pUC18 containing the erythromycin resistance gene from *S. erythreus* (Thompson et al., supra) inserted at the KpnI site.

Transformation of *Streptomyces lividans* with dhaB(1,2,3) and dhaT

The plasmids pDT13 or pDT14 were transformed into *Streptomyces lividans* TK23 using standard protoplast transformation techniques (Hopwood et al., *Genetic Manipulation of Streptomyces*, The John Innes Foundation (1985)). The transformants were selected on plates containing 50 µg/mL thiostrepton incubated at 30° C. Spores from the transformants were replated to obtain pure cultures.

Detection of Glycerol Dehydratase Activity

The *Streptomyces* transformants were grown in 25 mL of TSB (tryptone soy broth, Difco, Detroit, Mich.) plus 1% glucose, 2% glycerol, 1 mg/L vitamin $B_{12}$, 50 µg/mL thiostrepton at 30° C. for 3 days. The cells were harvested by centrifugation and resuspended in 1 mL of 100 mM Tris buffer, pH 7.4. The cells were broken using a French Press (20,000 psi) and the cell extract was assayed for glycerol dehydratase as described in GENERAL METHODS. Cell extract from *S. lividans* TK23 transformed with either pDT13 (Clone #8) or pDT14 (Clone #2) contained glycerol dehydratase with a specific activity of 0.1 U/mg.

Production of 1,3-propanediol in Recombinant *Streptomyces lividans*

*S. lividans* TK23/pDT14 (Clone #2) (ATCC 98052, also identified as *S. lividans* strain SL 14.2), inoculated from a TSA plate, was grown in 25 mL of TSB (Tryptone-Soy Broth, Difco, Detroit, Mich.) plus 1% glucose, 2% glycerol, 1 mg/L vitamin $B_{12}$, 50 µg/mL thiostrepton in a 250 mL flask. The shake-flask was incubated at 30° C. with vigorous shaking for three days, after which 3 mg/L 1,3-propanediol was detected by GC-MS analysis (TMS derivative) in the supernatant as described in GENERAL METHODS.

Example 16

Production of 1,3-propanediol from D-glucose using Recombinant *Streptomyces lividans*

Growth for demonstration of 1,3-propanediol production by *Streptomyces lividans* TK23 containing pDT13 or pDT14 proceeds aerobically at 30° C. in shake-flask cultures (erlenmeyer flasks, liquid volume 1/10th of total volume).

Cultures in rich media shake-flasks are started by inoculation from two-days old TSA-plates (trypticase soy agar, BBL #11043). Rich media are either TSB (trypticase soy broth; BBL #11768), Liquid Broth (which contains per liter: 16 g tryptone, 10 g yeast extract, and 5 g NaCl), medium B (TSB supplemented with per L: 10.0 g glucose, 2 mL Modified Balch's Trace-Element Solution in which NTA is replaced by citric acid, 2.0 g $Na_2CO_3$, 4.0 g $K_2HPO_4$, 1 mg vitamin $B_{12}$, final pH=7.2), or medium C (medium B, at pH 6.4). The composition of Modified Balch's Trace-Element Solution can be found in *Methods for General and Molecular Bacteriology* (P. Gerhardt et al., eds, p. 158, American Society for Microbiology, Washington, D.C. (1994)). Cultures in minimal media shake-flasks are started by inoculation from two-days old liquid TSB cultures, using a 1/30 (v/v) inoculum. Minimal media are either: MM322 (which contains per liter: 12.0 g glucose, 11.3 g $K_2HPO_4$, 1.0 g $(NH_4)_2SO_4$, 0.2 g Difco yeast extract, 0.1 g NaCl, 2 mg vitamin $B_{12}$ and 10 mL Modified Balch's Trace-Element Solution modified as above, final pH 6.7 (HCl)); medium D (medium MM322 supplemented with 2 g $Na_2CO_3$/L, final pH 7.2); or medium E (medium D, final pH 6.4). Media B and C and the minimal media are filter-sterilized, the other media are autoclaved.

The shake-flasks are incubated at 30° C. with vigorous shaking for two days, after which they are sampled for HPLC analysis of the supernatant. Glucose is added, the culture is incubated for 1 h under aerobic conditions, after which the culture is transferred to 25 mL volume glass tubes (which are nearly filled to the top). These tubes are subsequently incubated under anaerobic conditions at 30° C. After incubating for 2-5 days, 1,3-propanediol in the supernatant is detected by HPLC as described in GENERAL METHODS.

Example 17

Construction of General Purpose Plasmids, Plasmids for the Overexpression of dhaB(1-3) and dhaT in *Bacillus* and Production of 1,3-propanediol by Recombinant *B. licheniformis* and *B. subtilis*

Construction of General Purpose Expression Plasmids

The replicative high copy number shuttle vector pVS02 is used to co-express dhaB(1-3) and dhaT in *Bacillus*. pVS02 was constructed by cloning an EcoRI/BamHI fragment carrying an alkaline serine protease from *Bacillus lentus* fused to the *B. subtilis* apr promoter into pBS19. pBS19 is a derivative of pBS42 (Band and Henner, DNA 3, 17 (1984)) in which the EcoRI/BamHI fragment has been replaced by the EcoRI/HindIII polylinker from pUC19 (Boehringer Mannheim). To facilitate sequencing and PCR reactions, a 45 bp synthetic linker (SEQ ID NO:21) was introduced by PCR between the end of the protease gene and the transcriptional terminator.

The replicative low copy number shuttle vector pSS15-B is used to co-express dhaB(1-3) and dhaT in *Bacillus*. Plasmid pSS15-B was constructed by digesting plasmid pHP13 (Haima et al., *Mol. Gen. Genet.* 209, 335 (1987)) with HindIII/SalI (sites present in polylinker), filling the ends with T4 DNA Polymerase and religating to generate pSS13. A 2 kb EcoRI/BamHI fragment from pVS02 was inserted into the EcoRI/BamHI site of plasmid pSS13 to create pSS15-B.

Plasmids for the Over-Expression of dhaB(1-3) and dhaT Cassettes

In order to create a *Bacillus* consensus ribosome binding site at the 5' end of dhaT, an EcoRI/Xba linker obtained by annealing synthetic primers (SEQ ID NO:22 with SEQ ID NO:23) was inserted into the EcoRI/XbaI site of pAH23 to create pM17. A HindIII/BglII linker, using synthetic primers (SEQ ID NO:24 with SEQ ID NO:25) was added at the HindII/bglII site of plasmid pM17 to introduce a SalI site at the 5' end of dhaB1 to create pM20. The 0.3 kb MluI/KpnI fragment from plasmid pM20 was replaced with the 0.3 kb MluI/KpnI from plasmid pAH4 to introduce a HindIII site to create pM21.

A SalI-XbaI linker (SEQ ID NO:26 and 27) was inserted into pAH5 which was digested with the restriction enzymes, SalI-XbaI to create pDT15. The linker destroys the XbaI site and changes the reading frame so that the dhaT gene is fused to the open reading frame of protease coding sequence of plasmids pSS15-B and pVS2. The 1 kb SalI-MluI fragment from pDT15 was then inserted into pAH24, replacing the existing SalI-MluI fragment to create pDT17.

A SalI-XbaI linker (SEQ ID NO:28 and 29) was inserted into pAH5 which was digested with the restriction enzymes SalI-XbaI, to create pDT16. The linker destroys the XbaI site and changes the reading frame so that the dhaT gene is fused to the open reading frame of poly-His coding sequence of pUSH1 (Schon and Schuman, *Gene* 147, 91 (1994)). The 1 kb SalI-MluI fragment from pDT16 was then inserted into pAH24 replacing the existing SalI-MluI fragment to create pDT18.

Plasmid pDT4 (containing dhaB(1-3)) was constructed by introducing the 2.7 kb EcoRI/XbaI fragment from pDT2 into pUC18 (Boehringer Mannheim) digested with EcoRI/XbaI.

Plasmids for the Over-Expression of dhaT and dhaB(1-3) Cassettes in *Bacillus* pDT17 was digested with SacI, ends were filled with T4 DNA polymerase, and the DNA was digested with SalI to release the fragment containing dhaT and dhaB. The fragment was then ligated to pSS15-B digested with HindIII (ends blunted with T4 DNA polymerase) and SalI which created pM27.

Plasmids for the Over-Expression of dha B(1-3) in *Bacillus* using a lac-Based Inducible System A 2.7 kb BglII/HindIII fragment containing dhaB(1-3) from plasmid pDT4 was cloned into the HindIII/BamHI site in the polylinker of pUSH1 to create pM26. The dhaB1 gene was fused to the open reading frame of poly-His coding sequence of pUSH1.

Transformation of Plasmids into *Bacillus*

The plasmids pM26 and pM27 were transformed into *B. licheniformis* BG307 by natural transformation (McCuen and Thome, *J. Bacteriol.* 107, 636-645 (1971)) and selected on 10 ug/mL kanamycin and 30 ug/mL chloramphenicol, respectively. The same plasmids were transformed into *B. licheniformis* strain BG188 using standard protoplast transformation techniques (Pragai et al., *Microbiology,* 140, 305 (1994)) and selected as above. *B. subtilis* strains BG2864 was transformed with the plasmid pM27 by natural transformation. Transformants containing plasmids were selected on LA plates containing 10 ug/mL chloramphenicol.

Plasmid pM26 was also transformed into *B. subtilis* strain 1E62 (Saito et al., *Mol. Gen. Genet.,* 170, 117 (1979)) and transformants containing plasmids were selected on LA plates containing 10 ug/mL erythromycin and 20 ug/mL kanamycin.

All transformants were grown at 30° C.

Detection of Glycerol Dehydratase Activity

*B. licheniformis* strain BG188 transformed with pM26 (Clone #8) was grown in 25 mL of LB (Difco) plus 1% glucose and 10 ug/mL kanamycin at 30° C. overnight. The cells were harvested by centrifugation and resuspended in 1 mL of 0.1 M Tricine/KOH buffer, pH 8.2, 50 mM KCl, 1 mM dithiothreitol and 200 uM phenylmethylsulfonyl fluoride. Cell extract was obtained by breaking the cells in the French Press (20,000 PSI) and analysis for glycerol dehydratase was performed as described in GENERAL METHODS. A specific activity of 0.036 U/mg was obtained. The specific activity of 1,3-propanediol dehydrogenase, measured as described in GENERAL METHODS, was 0.2 U/mg.

Production of 1,3-propanediol in Recombinant *Bacillus*

*B. licheniformis* strain BG188 transformed with pM26 (Clone #8) (ATCC 98051) was grown in a shake flask containing 25 mL of LB (Difco) plus 1% glucose and 10 ug/ml kanamycin at 30° C. overnight with vigorous shaking, after which 1 mL was used to innoculate 25 mL of LB plus 1% glucose, 1% glycerol, 0.33 ug/mL vitamin $B_{12}$, and 10 ug/mL kanamycin in a 250 mL flask. Shake flasks were incubated at 30° C. with vigorous shaking and after 9 h of growth 300 ug/L 1,3-propanediol was detected by GC/MS (TMS derivitization) as described in GENERAL METHODS.

*B. subtilis* strain BG2864 transformed with pM27 (clone #1) (ATCC 98050) was grown in a shake flask containing 25 mL of LB plus 1% glucose, 1% glycerol, 0.33 ug/mL vitamin $B_{12}$, and 10 ug/mL chloramphenicol in a 250 mL flask. Shake flasks were incubated at 30° C. with vigorous shaking and after 43 h of growth, 1,3-propanediol was detected.

Production of 3-hydroxypropionaldehyde by Recombinant *Bacillus*

*Bacillus* fermentations were carried out in 15.5 L total volume Biolafitte fermenters, working volume initially 7 liters, increasing to 9.5 liters during the run. Aerobic conditions were insured by aeration with air at a rate of 7 liters/minute, at an impeller speed of 650 rpm and a back-pressure of 0.8 bar (aerobic conditions are defined by the % Dissolved Oxygen (100% DO defined at ambient pressure), measured with installed DO-probes; a minimal value of 35% DO was considered aerobic). The pH was maintained at 6.70 by automatic addition of 10% $H_2SO_4$ or 28% $NH_4OH$. Temperature was maintained at 30° C.

The following compounds were batched into the tank and sterilized at 121° C. for 30 minutes: (gram per liter) 6 $NaH_2PO_4 1H_2O$, 10 $K_2HPO_4$, 1.5 NaCl, 10 $(NH_4)_2SO_4$, 0.2 $FeCl_3$, 1.5 tryptone, 6 yeast extract, 10 mL of Balch's modified trace-element solution (*Methods for General and Molecular Bacteriology* (P. Gerhardt et al., eds) p. 158, American Society for Microbiology, Washington, D.C. (1994)) and 2 MAZU DF204 (a custom-made antifoam). After sterilization, 350 gram of the 50% glucose feed was added, together with kanamycin and chloramphenicol (both up to a final concentration of 10 mg/liter).

0.6 liter of a 24 hours old *Bacillus licheniformis* BG118/ pM26 (clone #8) shakeflask, growing in LBG1% (=10 g tryptone, 5 g yeast extract, 5 g NaCl, 10 g glucose), was used to inoculate the fermenter. The culture was then allowed to grow and exhaust the glucose; a pH rise over 6.60 triggered the glucose feed (50% glucose, autoclaved, at a rate of 0.7 gram/minute). After 45 hours, a nutrient addition was made (50 ml Balch's trace element solution, 14 gram $K_2HPO_4$, 14 gram yeast extract, 14 ml vitamin solution, pH set at 6.60, filter-sterilized). After 70 hours, vitamin B 12 was added up to a final concentration of 10 mg/L. The % DO was kept at aerobic levels for the first 92 hours. Glucose was present in (small) excess throughout the run (0.2-12 g/L during the aerobic part (first 92 hours); 0.2-36 g/L during the $O_2$-limited part (from 92-164 hours)). In a sample taken at 87 hours, the presence of 3-hydroxypropionaldehyde was suspected and confirmed by detection of 1,3-propanediol after treating the supernate sample with the reducing agent sodium borohydride.

Example 18

Alternate Plasmids for the Over-Expression of dhaT and dhaB(1-3) cassettes in *Bacillus*

Plasmids for the Over-Expression of dhaT and dhaB(1-3) Cassettes in *Bacillus*

A SalI/HindIII fragment from plasmid pM21, containing dhaB(1-3) and dhaT, is ligated with the 5 kb Sal/HindIII pVS02 vector to create pM22. pM22 has dhaB and dhaT under the apr promoter in a high copy number vector.

A SalI/HindIII fragment from plasmid pM21, is ligated with the 5.8 kb Sal/HindIII fragment from pSS15-B to create pM23. pM23 has dhaB and dhaT under the apr promoter in a low copy number vector.

Plasmids for the Over-Expression of dhaT and dhaB(1-3) Cassettes in *Bacillus* pDT17 is digested with SacI, ends are filled with T4 DNA polymerase, and the DNA is digested with SalI to release the fragment containing dhaT and dhaB. The fragment is then ligated to pVS02 digested with HindIII (ends blunted with T4 DNA polymerase) and SalI which created pM25.

Plasmids for the Over-Expression of a dhaT and dha B(1-3) Cassette in *Bacillus* using a lac-Based Inducible System.

pDT18 was digested with SacI, ends were filled with T4 DNA polymerase, and DNA is digested with SalI to release the fragment containing dhaT and dhaB, both genes containing a *Bacillus* consensus ribosome binding site. The fragment is then ligated to pUSH1 (Schon and Schuman, supra) digested with HindIII (ends blunted with T4 DNA polymerase) and SalI to create pM24.

Example 19

Conversion of D-glucose to 1,3-propanediol by Recombinant *Bacillus*

Growth Conditions for *Bacillus*

Growth for demonstration of 1,3-propanediol production by *Bacillus licheniformis* and *Bacillus subtilis* proceeds aerobically at 30° C. or 35° C. (as indicated) in shake-flask cultures (erlenmeyer flasks) and in 15.5 L (total volume) Biolafitte fermenters (working volume 7-10 L).

Cultures in LBG (which contains per L: 16 g tryptone, 10 g glucose, 10 g yeast extract, and 5 g NaCl) shake-flasks are started by inoculation from one-day old TSA-plates (Trypticase Soy Agar, BBL #11043). These shake-flasks are then used to inoculate either fermenters or shake-flasks in which the demonstration proper of D-glucose to 1,3-propanediol conversion is demonstrated.

Batch Cultures in Shake-Flasks

Rich media are either TSB (trypticase soy broth; BBL #11768), LBG, medium B (TSB supplemented with per L: 10.0 g glucose, 2 mL Modified Balch's Trace-Element Solution in which NTA is replaced by citric acid, 2.0 g $Na_2CO_3$, 4.0 g $K_2HPO_4$, 1 mg vitamin B12, final pH=7.2), or medium C (medium B, at pH 6.4). The composition of Modified Balch's Trace-Element Solution can be found in *Methods for General and Molecular Bacteriology* (P. Gerhardt et al., eds., p. 158, American Society for Microbiology, Washington, D.C. (1994)). Minimal media are either: MM322 (which contains per liter: 12.0 g glucose, 11.3 g $K_2HPO_4$, 1.0 g $(NH_4)_2SO_4$, 0.2 g Difco yeast extract, 0.1 g NaCl, 2 mg vitamin $B_{12}$ and 10 mL Modified Balch's Trace-Element Solution modified as above, final pH 6.7 (HCl)); medium ID (medium MM322 supplemented with 2 g/L $Na_2CO_3$, final pH 7.2); or medium E (medium D, final pH 6.4). Media 8 and C and the minimal media are filter-sterilized, the other media are autoclaved.

The shake-flasks are incubated at 30° C. with vigorous shaking for one day, after which they are sampled for HPLC analysis of the supernatant. Glucose is added, the culture is incubated for 1 hr under aerobic conditions, after which the culture is transferred to 25 mL volume glass tubes (which are nearly filled to the top). These tubes are subsequently incubated under anaerobic conditions at 30° C. After incubation for 1-5 days, 1,3-propanediol in the supernatant is detected by HPLC as described in GENERAL METHODS.

Batch and Fedbatch Cultures in Fermenters

A 600-mL total volume culture from a shake-flask (LBG medium) is used to inoculate a fermenter with 6.4 L of medium, batched in and autoclaved for 30 minutes (minimal media) or 45 min (rich media) Typical minimal media in the fermenter is medium D, typical 'rich' media is media D with an additional 50 g yeast extract/L. Filter-sterilized additions (vitamin $B_{12}$ or compensations for auxotrophy) are performed after the fermenter has been autoclaved, using a syringe and a septum-port in the fermenter lid.

Back pressure (BP, 0.1-0.5 bar), aeration (L of air per min, 0.4-1 vvm), stirring (rpm, 200-600), temperature (T, 30-37° C.), Dissolved Oxygen (% DO), and pH (5.8-7.2, by $NH_4OH$ and $H_2SO_4$ or $H_3PO_4$ addition) are monitored and controlled at the desired values, as indicated.

After inoculation, the cells are grown in batch mode for the first 14 h, after which a glucose feed is started. For anaerobic growth/production, the % DO is allowed to go to 0% by either reduction of rpm and BP, additionally by replacing the air going in by $N_2$, as indicated.

Fermenters and shake-flasks are sampled for $OD_{550}$ readings (growth) and an enzymatic glucose assay on the supernate; supernate is also prepared for HPLC analysis via our standard procedure, as outlined in GENERAL METHODS. 1,3-Propanediol is present in the supernatant.

Example 20

Transformation of *Pseudomonas* with dhaB(1,2,3) and dhaT and Demonstration of 1,3-propanediol Production Construction of Plasmids for Co-Expression of dhaB(1,2,3) and dhaT in *Pseudomonas*

The 4.1 kb expression cassette for dhaB(1,2,3) and dhaT from pAH27 was inserted into the vectors pMMB66EH (Füste et al., *Gene*, 48, 119 (1986)) and pMMB207 (Morales et al., *Gene*, 97, 39 (1991)) using the restriction enzymes EcoRI and SalI to create pDT10 and pDT9, respectively.

Transformation of *P. aeruginosa* PAO 2845 with the pDT9 Expression Plasmid

*P. aeruginosa* PAO 2845 cells were prepared for transformation by overnight growth at 37° C. with shaking at 200 rpm in L-broth. A 1:25 inoculation of the culture was made into 25 mL of fresh prewarmed and preaerated L-broth. The fresh culture was incubated 2-3 h to early log phase at 37° C. and 200 rpm. The cells, collected by centrifugation, were washed twice in 10 mL of ice cold 0.15 M $MgCl_2$ containing 5% dimethylsulfoxide and resuspended in 2 mL of the dimethylsulfoxide solution. The cell suspension (0.2 mL) was combined with 100-200 ng pDT9 DNA and placed on ice for 60 min. The reaction mixture was heat shocked at 37° C. for 2 min and transferred to ice for 5 min. L-broth (0.5 mL) was added and the cells were incubated for 20 min at 37° C. Single colonies were obtained from nutrient agar plates supplemented with 37.5 ug/mL chloramphenicol.

Conjugal Transfer of pDT10 into *P. aeruginosa* PAO1

The plasmid, pDT10 was mated into PAO1 by the method of Figurski and Helinski (*Proc. Natl. Acad. Sci. U.S.A.*, 76, 1648 (1979)). pDT10 was transformed into *E. coli* AC80 (Chakrarty et. al., *Proc. Natl. Acad. Sci. U.S.A.*, 75, 3109 (1978)) to create a donor strain. The helper strain was *E. coli* HB101 containing pRK2013 (Figurski and Helinski, supra). The recipient strain was *Pseudomonas aeruginosa* PAO1 (Royle et al., *J. Bacteriol.*, 145, 145 (1981)). Cultures (5 mL) of each of the strains were grown overnight in LB at 37° C. The cells were washed in 0.9% NaCL and resuspended in 200 µL. The cells were mixed together and spread on a LA plate (Luria Agar, Difco). The plate was incubated at 37° C. for 6 h. The cells were removed from the plate and transferred to PIA (Difco) plates containing 250 µg/mL carbencillin and grown overnight. Single colonies were isolated on the same media Detection of Glycerol Dehydratase and 1,3-propanediol Dehydrogenase Activity

*Pseudomonas aruginosa* PAO1/pDT10 was grown in 25 mL 2XYT (16 g/L yeast extract, 16 g/L tryptone, 5 g/L NaCl) plus 250 µg/mL carbenicillin, 0.1 mM IPTG overnight at 37° C. The cells were harvested by centrifugation and resuspended in 1 mL of 100 mM Tris buffer pH 7.4. The cells were broken by French Press at 15,000 psi. The crude extract was then assayed for glycerol dehydratase and 1,3-propanediol dehydrogenase activity using standard assays. Protein determination was by Bio-Rad (Bradford) Protein Assay. Specific activity for glycerol dehydratase was 5 U/mg. Specific activity for 1,3-propanediol dehydrogenase was 20 U/mg. Similarly prepared, crude extract from *P. aeruginosa* PAO 2845 transformed with pDT9 contained 0.05 U/mg glycerol dehydratase activity.

Production of 1,3-propanediol by *Pseudomonas aeruginosa* Containing the pDT9 Plasmid

*Pseudomonas aeruginosa* PAO 2845 containing the pDT9 plasmid (ATCC 55760) was grown overnight at 37° C. and 200 rpm shaking in 2XYT medium supplemented with 25 µg/mL chloramphenicol. Following overnight growth, an aliquot of the cell suspension was transferred to growth medium (3 parts 2XYT medium+1 part HEPES0.1 medium, supplemented with 0.25% (w/v) glucose, 0.2% (w/v) $KNO_3$, 25 µg/mL chloramphenicol, 50 mg/L yeast extract, and 80 mg/L nutrient broth) resulting in a cell suspension with an $OD_{660}$ nm of 0.5-0.8 AU. HEPES0.1 medium contains the following components: $NH_4Cl$, 9.52 mM; $MgCl_2.6H_2O$, 0.523 mM; $K_2SO_4$, 0.276 mM; HEPES (N-[2-hydroxyethyl] piperazine-N-[2-ethanesulfonic acid]), 40 mM; tricine (N-tris (hydroxymethyl)methyl glycine), 4 mM; $FeSO_4.7H_2O$, 0.010 mM; $K_2HPO_4$, 0.132 mM; and, trace minerals to give final concentrations of the following components in g/L: sodium citrate-$6H_2O$, 0.001; $FeSO_4.7H_4O$, 0.0005; $CoCl_2.6H_2O$, 0.0001; $MnCl_2.4H_2O$, 0.00001; $ZnCl_2$, 0.000005; $Na_2MoO_4.2H_2O$, 0.000025; $NiCl_2.6H_2O$, 0.0001; $CuSO_2.2H_2O$, 0.00005. After approximately 1 h of growth at 30° C. with shaking at 250 rpm, 0.5 mM IPTG (isopropyl-β-D-thiogalactoside) was added to the growth medium and cell growth was continued. After approximately 5 h of additional growth, cells were harvested by centrifugation at room temperature. Cells were washed 3x with production medium: HEPES0.1 medium supplemented with 0.25% (w/v) glucose, 0.2% (w/v) $KNO_3$, 25 µg/mL chloramphenicol, 50 mg/L yeast extract, and 80 mg/L nutrient broth. In duplicate, the washed cells were suspended at the original harvested volume in production medium containing 0.2% (v/v) glycerol. Cell suspensions were incubated under a nitrogen atmosphere at 30° C. with shaking at 250 rpm. After approximately 1 h, 5 µg/mL coenzyme $B_{12}$ (5,6-dimethyl-benzimidazolylcobamide 5-deoxyadenosine) was added to the cell suspension and the incubation continued at 30° C. with shaking at 250 rpm. Samples of the cell suspension were collected periodically for product analysis. Upon collection, cells were removed from the samples by centrifugation and the aqueous supernatant stored frozen, −20° C., until analyzed.

Analysis by HPLC with calibrations based on authentic standards showed that these cell suspensions produced 1,3-propanediol. The results are shown in Table 15. The identity of the product was confirmed by GC/MS analysis as described in the GENERAL METHODS.

TABLE 15

Production of 1,3-propanediol by *Pseudomonas aeruginosa* containing the pDT9 plasmid

| Sample | Time (hr) | 1,3-Propanediol (mM) |
|---|---|---|
| A | 0 | 0 |
| A | 24 | 5.1 |
| B | 0 | 0 |
| B | 24 | 5.6 |

Example 21

Production of 1,3-propanediol from D-glucose using *Pseudomonas aeruginosa*

General Growth Conditions

*Pseudomonas aeruginosa* strain PAO2845 from PGSC (*Pseudomonas* Genetic Stock Center, East Carolina School of Medicine, Greenville, N.C.) is grown in basal medium, HEPES0.1, which the following components: $NH_4Cl$, 9.52 mM; $MgCl_2.6H_2O$, 0.523 mM; $K_2SO_4$, 0.276 mM; HEPES (N-[2-hydroxyethyl]piperazine-N-[2-ethanesulfonic acid]), 40 mM; Tricine (N-tris (hydroxymethyl)methyl glycine), 4 mM; $FeSO_4.7H_2O$, 0.010 mM; $K_2HPO_4$, 0.132 mM; and trace minerals to give final concentrations of the following components in g/L: sodium citrate-$6H_2O$, 0.001; $FeSO_4.7H_4O$, 0.0005; $CoCl_2.6H_2O$, 0.0001; $MnCl_2.4H_2O$, 0.00001; $ZnCl_2$, 0.000005; $Na_2MoO_4.2H_2O$, 0.000025; $NiCl_2.6H_2O$, 0.0001; $CuSO_2.2H_2O$, 0.00005. HEPES0.1 is used in all experiments; supplementations are noted where they occur.

Construction of a Glycerol Negative Mutant of *P. aeruginosa* PAO 2845 by Gene Interruption

*P. aeruginosa* PAO 2845 is grown overnight in Nutrient Broth (Difco, Detroit, Mich.) at 37° C. and 200 rpm shaking. Cells are recovered by centrifugation and DNA extracted from cells using a standard alkaline lysis procedure (Sambrook 1989). The open reading frame for glpR (glycerol catabolism regulatory protein gene, Genbank ACCESSION # M60805) is amplified from *P. aeruginosa* PAO 2845 by PCR using primers JJ-gplR-5' and JJ-glpR-3' (SEQ ID NOS:30 and 31, respectively), incorporating EcoRI sites at the 5' ends. This DNA fragment is then ligated into plasmid pARO180 (Parke, Gene 93, 135, (1990)) at its unique EcoR1 restriction site resulting in plasmid pJJ10. *E. coli* transformed with DNA from the pJJ10 ligation mix are spread on Nutrient Agar (Difco, Detroit, Mich.) containing 50 µg/mL ampicillin and 0.08 mg/mL Xgal (5-bromo-4-chloro-3-indolyl-β-D-galactoside). White colonies, indicating a high probability of glpR insertion, are picked and transferred to LB medium supplemented with 50 µg/mL ampicillin. From cells harvested after overnight growth at 37° C. and 200 rpm shaking, pJJ10 DNA is recovered.

The kanamycin cassette region from pUC4K (Pharmacia Cat. No. 27-4958-01) is amplified by PCR using primers (SEQ ID NO:32 AND 33) appropriately designed to amplify the region and modify the termini of the fragment to be compatible with restriction enzyme Sty1 (Promega, Madison, Wis.) resulting in the 4 kb fragment pUC4K-sty1. The pUC4K-sty1 DNA fragment is subcloned into the Sty1 site within the glpR gene of plasmid pJJ10, generating plasmid pJJ11. *E. coli* transformed with DNA from the pJJ11 ligation mixture are spread on LB agar supplemented with 25 µg/mL kanamycin and 50 µg/mL ampicillin. DNA from 5-20 isolated colonies is individually collected following overnight growth at 37° C. in LB medium supplemented with 25 µg/mL kanamycin and 50 µg/mL ampicillin. The presence of the desired plasmid DNA is confirmed by gel electrophoresis.

*P. aeruginosa* PAO 2845 is transformed with pJJ11 DNA following standard protocols. Briefly, *P. aeruginosa* cells are prepared for transformation by overnight growth at 37° C. with shaking at 200 rpm in L-broth. A 1:25 inoculation of this overnight culture is made into 25 mL of fresh prewarmed and preaerated L-broth. The fresh culture is incubated for 2-3 h (to early log phase) at 37° C. and 200 rpm. Cells are centrifuged and supernatant decanted. Collected cells are resuspended in 10 mL of ice cold sterile 0.15 M $MgCl_2$ containing 5% dimethylsulfoxide and held on ice for 5-10 min. Cells are centrifuged, separated from the supernatant and resuspended in 10 mL of ice cold sterile 0.15 M $MgCl_2$ containing 5% dimethylsulfoxide and held on ice for 5-10 min. After a final centrifugation and separation from the supernatant, the cells are resuspended in 2 mL of ice cold sterile 0.15 M $MgCl_2$ containing 5% dimethylsulfoxide. A 0.2 mL aliquot of the cold cell concentrate is combined with 100-200 ng pJJ11 DNA in a prechilled 1.5 mL polypropylene centrifuge tube and the mixture is held on ice for 60 min. The tube is then rapidly transferred to a 37° C. water bath for 2 min and immediately returned to ice for 5 min. Approximately 0.5 mL of L-broth is added and the cells are incubated for 0.3-1 hour with gentle shaking at 37° C. Following the recovery incubation, 10 µL and 50 µL aliquots of the cell suspension are spread on nutrient agar plates supplemented with 50 µg/mL kanamycin. Colonies developing on the selective medium are screened for growth on agar plates with HEPES0.1 medium supplemented with 1% succinic acid or 1% glycerol. Clones unable to grow on glycerol, but capable of growth on succinate, are preserved for later use by freezing in 15% glycerol.

Transformation of gplR$^-$ *P. aeruginosa* PAO 2845 with pDT9

*P. aeruginosa* is prepared for transformation by the method described above. A 0.2 mL aliquot of the cold cell concentrate is combined with 100-200 ng pDT9 DNA in a prechilled 1.5 mL polypropylene centrifuge tube and the mixture held on ice for 60 min. The tube is then rapidly transferred to a 37° C. water bath for 2 min and immediately returned to ice for 5 min. Approximately 0.5 mL of L-broth and cells are incubated 0.3-1 h with gentle shaking at 37° C. Following the recovery incubation, 10 µL and 50 µL aliquots of the cell suspension are spread on nutrient agar plates supplemented with 37.5 µg/mL chloroamphenicol.

Screening of glpR$^-$ *P. aeruginosa* PAO 2845 Transformants for the Presence pDT9

The transformants from above are plated on nutrient agar plates supplemented with 37.5 µg/mL chloramphenicol grown overnight at 37° C. From the colonies appearing on these selective plates, approximately twenty are picked and transferred to 10 mL Nutrient Broth (Difco, Detroit, Mich.) containing 37.5 µg/mL chloramphenicol and grown overnight at 37° C. and 200 rpm shaking. To confirm the presence of the pDT9 plasmid in the selected transformants, plasmid DNA is extracted, purified and cut with EcoRI (Promega, Madison, Wis.). The molecular weight of the linearized DNA is analyzed by gel electrophoresis. In addition, PCR amplification using primer pairs with sequences common to dhaT, dhaB1, dhaB2, and dhaB3 (SEQ ID NO:34 AND 35, 36 AND 37, 8 AND 9, 4 AND 5, respectively) followed by fragment molecular weight characterization using gel electrophoresis is used to confirm the presence of the desired genes.

Metabolic Screening of glpR$^-$ *P. aeruginosa* PAO 2845 transformed with pDT9

One to twenty clones are selected from the positive transformants above for further characterization. Cells are grown aerobically on Nutrient Broth supplemented with 37.5 µg/L chloramphenicol overnight at 30° C. with shaking at 250 rpm. Cells are transferred at a 1:8 dilution into the same medium with 1.5 mM IPTG (isopropyl-β-D-thiogalactoside) and grown for 4-6 h. Cells are then harvested by centrifugation and washed once with HEPES0.1 medium supplemented with 10 g/L glycerol, 0.03 g/L beef extract, 0.05 g/L peptone, 0.05 g/L yeast extract (all Difco, Detroit, Mich.) and 0.2% $KNO_3$. The cells are then resuspended at ⅕ the original volume, with no air space, in a small vial and incubated at 30° C. with shaking at 100 rpm for 18-72 h. Cells are removed by centrifugation and the supernatants analyzed for the presence of 1,3-propanediol by HPLC. In addition, the chemical identity of 1,3-propanediol is confirmed by gas chromatography-mass spectrometry.

Production of 1,3-propanediol from Glucose by glpR⁻ *P. aeruginosa* PAO 2845 Transformed with pDT9 (ATCC 55760)

From the screening procedure above, one to five clones which produce the greatest amount of 1,3-propanediol from glycerol are grown aerobically on nutrient broth supplemented with 37.5 µg/L chloramphenicol overnight at 30° C. with shaking at 250 rpm. Cells are transferred at a 1:8 dilution into the same medium with 1.5 mM IPTG, allowed to grow for 4-6 h, harvested by centrifugation and washed once with HEPES0.1 medium supplemented with 10 g/L glucose, 0.03 g/L beef extract, 0.05 g/L peptone, 0.05 g/L yeast extract and 0.2% $KNO_3$. The cells are then resuspended at ⅕ the original volume, with no air space, in a small vial. Cells are incubated at 30° C. with shaking at 100 rpm for approximately 36 h. Cells are removed by centrifugation and the supernatants analyzed for the presence of 1,3-propanediol by HPLC. In addition, the chemical identity of 1,3-propanediol is confirmed by gas chromatography-mass spectrometry.

Example 22

Construction of Expression Cassettes for Expression of dhaB1, dhaB2, dhaB3 and dhaT in *Aspergillus niger*

General Expression Cassette (pAEX):

The 1.4 kb Spe1-EcoRV fragment from the plasmid pGPT-pyrG (Berka et al., "The development of gene expression systems for filamentous fungi", *Biotechnol. Adv.*, 7:127-154 (1989)), containing sufficient portions for proper regulation of the *Aspergillus niger* gla A promoter and terminator, was ligated into the SpeI and EcoRV sites in the polylinker of pLITMUS39 (New England Biolabs, Beverly, Mass.).

Individual Clone Expression Cassettes for *A. niger*:

The open reading frames (ORF's) for individual *Klebsiella pneumoniae* dhaB subunits and dhaT were cloned and ligated into the general expression vector (pAEX) separately, using the same cloning strategy:

Primer pairs for PCR amplification of each individual dhaB ORF and the dhaT ORF were designed to match the 5' and 3' ends sequence for each ORF based on known sequence of the entire gene operon (dhaB1, dhaB2, dhaB3, dhaBX and dhaT: SEQ ID NO:38 and 12, 39 and 40, 41 and 42, 45 and 46, 43 and 44, respectively). In addition to the matching sequence, the primers for the 5' end of each ORF were designed to include an EcoR1 restriction site followed by a Bgl II restriction site at the 5' most end of the sequence as well as the five base sequence CAGCA upstream of the first ATG of each ORF. Primers designed to match the 3' ends of each ORF placed an Xba1 restriction site downstream of the translation stop codon, at the 3' most end of the clone.

Individual clone fragments for the dhaB and dhaT ORF's were amplified by PCR from the plasmid pHK26-28, containing the entire *K. pneumoniae* dha operon, using the primers described above. The individual ORF clone fragments were isolated based on their respective molecular weights (dhaB1=1540 bp; dhaB2=607 bp; dhaB3=448 bp; dhaBX=1846 bp; dhaT=1187 bp). Using the unique EcoR1 and Xba1 restriction sites designed in the PCR primers, each individual dhaB and dhaT ORF fragment was ligated into the EcoR1 and Xba1 restriction sites in the polylinker of pLITMUS29 (New England Biolabs). The dhaB2 and dhaB3 clones in pLITMUS29 were confirmed to be correct by sequencing. A unique 1363 bp Nco1-EcoRV restriction fragment from the coding region of dhaB1 clone in pLITMUS29 was removed and replaced with the corresponding restriction fragment from pHK26-28. A unique 783 bp Tth111 I-Mlu I restriction fragment from the coding region of dhaT clone in pLITMUS29 was replaced with the corresponding restriction fragment from pHK26-28. A unique 1626 bp EcoRV restriction fragment from the coding region of dhaBX clone in pLITMUS29 was replaced with the corresponding restriction fragment from pM7 (containing the *K. pneumoniae* dhaB operon). The 5' and 3' end sequences of the dhaB1, dhaBX and dhaT clones, approximately 250 bp which includes some sequence from the substituted fragment, was confirmed to be correct by sequencing.

The unique Bgl II-XbaI restriction fragments containing the ORF's of dhaB1, dhaB2, dhaB3, dhaBX and dhaT clones in pLITMNS29 were ligated into the Bgl II-XbaI restriction sites in the general expression vector pAEX separately, placing expression of each clone under the control of the *A. niger* glaA promoter and terminator. Each resulting vector was named by the respective ORF, i.e.: pAEX:dhaB1, pAEX:dhaB2, pAEX:dhaB3, pAEX:dhaBX and pAEX:dhaT.

Dual Expression Cassette Vectors for *A. niger*:

The unique SnaB1-Stu1 restriction fragment containing the dhaB1 expression cassette (consisting of the *A. niger* glaA promoter, the dhaB1 ORF, and terminator) was isolated from the vector pAEX:dhaB1 and ligated into the unique SnaB1 restriction site in the pAEX:dhaB2 vector. The approx. 2.2 kb Sca1-Sma1 restriction fragment from pBH2 (Ward et. al., *Exp. Myc.*, 13, 289 (1989)) containing the *Aspergillus nidulans* pyrG auxotrophy selectable marker, was ligated into the unique Stu1 restriction site in the vector containing the dhaB1 and dhaB2 expression cassettes. This vector was named pAEX:B1+B2.

The unique Spe1-Hind III in restriction fragments containing the entire expression cassettes for dhaB3 and dhaT were isolated from the respective pAEX:dhaB3 and pAEX:dhaT vectors. The two expression cassette fragments were simultaneously ligated, in tandem, in the unique Hind III restriction site in the vector pUC18. This vector was named pAEX:B3+T.

Transformation Isolation of Transformants Confirmation of Integration of Expression Cassettes and Expression of dhaB and dhaT Genes in *Aspergillus*

*Aspergillis niger* strain FS1 (pyrG⁻) was co-transformed with the two expression vectors pAEX:B1+B2 and pAEX:B3+T using the method of (Campbell et al., "Improved transformation efficiency of *A. niger* using homologous niaD gene for nitrate reductase", *Curr. Genet.*, 16:53-56 (1989)). Transformants were selected for by their ability to grow on selective media without uridine. Genomic DNA of transformants was digested with Hind III and Spe1 to liberate fragments of predicted molecular weights, demonstrating integration of intact expression cassettes. Detection of each expression cassette was done by Southern analysis, probing with individual genes separately. The presence of the dhaB2 protein was detected by western analysis using anti-dhaB antibody.

Expression of each ORF was tested by growing transformants, that have the pAEX:B1+B2 and pAEX:B3+T vectors integrated, in 10% CSL media (corn steep liquor (50% solids), 10% (w/v); $NaH_2PO_4H_2O$, 1.0 g/L; $MgSO_4$, 0.50 g/L;

maltose, 100.0 g/L; glucose, 10.0 g/L; and Mazu Antifoam, 0.003% (v/v)) as a seed culture then transferring 1/10 volume of the seed culture to MBM carbon media (NaH$_2$PO$_4$, 0.70 g/L; K$_2$HPO$_4$, 0.70 g/L; KH$_2$PO$_4$, 0.70 g/L; MgSO$_4$.7H$_2$O, 1.40 g/L; (NH$_4$)$_2$SO$_4$, 10.5 g/L; CaCl$_2$.2H$_2$O, 0.70 g/L; NH$_4$NO$_3$, 3.50 g/L; sodium citrate, 14 g/L; FeCl$_2$.4H$_2$O, 1.0 mg/L; ZnCl$_2$, 5.87 mg/L; CuCl$_2$, 2H$_2$O, 0.42 mg/L; MnCl$_2$, 4H$_2$O, 0.21 mg/L; Na$_2$B$_4$O$_7$.10H$_2$O, 0.07 mg/L; folic acid, 0.174 mg/L; pyridoxine-HCl, 6.12 mg/L; riboflavin, 1.83 mg/L; pantothenic acid, 23.60 mg/L; nicotinic acid, 26.66 mg/L; biotin, 0.49 mg/L; thiamine-HCl, 1.39 mg/L; maltose, 120.0 g/L; carbenicillin, 0.035 mg/L; streptomycin, 0.035 mg/L; tween 80, 0.07% (w/v); and Mazu antifoam, 0.14% (v/v)) for induction of the glaA promoter. mRNA was isolated from transformant cultures (Fast Track 2 Kit, Invitrogen Corp.) and Northern analysis performed with chemiluminescence (Genius® System, Boehringer-Mannheim) to detect transcribed message from each gene. Co-ordinate transcription of the dhaB1, dhaB2, dhaB3 and dhaT genes in shake flask cultures was demonstrated by Northern hybridization, probing with gene fragments of each dhaB and dhaT ORF.

Isolated colonies shown to transcribe all of the transformed genes were chosen to be further transformed with pAEX: dhaBX. These isolates were co-transformed with pAEX: dhaBX and pAA10 (3.2 kb. Acc1-Asp718 restriction fragment containing the *Aspergillus nidulans* amdS selectable marker in pUC18). These newly transformed cultures were selected for on media containing acetamide as the sole carbon source. Transformant colonies able to utilize acetamide as a sole carbon source were demonstrated to have the dhaBX ORF integrated by PCR amplification of the dhaBX ORF from genomic DNA using primers KpdhaBX-5' and KpdhaBX-3' (SEQ ID NO:45 and 46).

Production of Glycerol by *A. niger*, Strain FS1

*Aspergillus niger* strain FS1 was grown in 10% CSL media as a seed culture and transferred as a 1:10 dilution to MBM carbon media+12% maltose. Culture supernatent was demonstrated to contain 6 g/L glycerol produced by *Aspergillus*. Analysis of glycerol was done by HPLC.

Production of 1,3-propanediol by Recombinant *A. niger*

*Aspergillus* fermentations were carried out in 15.5 L total volume Biolafitte fermenters, working volume initially 8 L, increasing to 11 L during the run. Aerobic conditions were insured by aeration with air at a rate of 10 L/min., at an impeller speed of 700-800 rpm and a back-pressure of 1.1 bar (aerobic conditions are defined by the % Dissolved Oxygen (100% DO defined at ambient pressure), measured with installed DO-probes; a minimal value of 35% DO was considered aerobic). The pH was maintained at 5.60 by automatic addition of 10% H$_3$PO$_4$ or 28% NH$_4$OH. Temperature was maintained at 32° C.

The following compounds were batched into the tank and sterilized at 121° C. for 30 min.: 2 g/L NaH$_2$PO$_4$.H$_2$O, 17 g/L (NH$_4$)$_2$SO$_4$, 1 g/L MgSO$_4$, 2 g/L Tween 80, 45 g/L Promosoy-100 (a soy concentrate of 70% protein), 6 µL corn steep liquor (50% solids), 10 g/L maltose, and 2 g/L MAZU DF204 (a custom-made antifoam). After sterilization, 500 gram of the 50% Maltrin 150 feed was added, together with carbenicillin and streptomycin (both up to a final concentration of 10 mg/L).

One liter of a 45 hold *Aspergillus niger* strain (strain TGR40) transformed with the two expression vectors pAEX: B1+B2 and pAEX:B3+T, growing in a shakeflask containing 10% CSL was used to inoculate the fermenter. The culture was then allowed to grow batchwise, fully aerobic, for 28 h before a feed (a 50% Maltrin 150 solution, heat sterilized) was started at a rate of 0.8-1.0 g/min. The culture was then run for another 20 h, during which the % DO dropped to virtually zero because of the O$_2$-demand of the cells (the culture remained at zero to 5% throughout the rest of the run). After that (48 h after inoculation), glycerol was fed in over a period of 8 h, up to a final glycerol concentration of 163 g/L. The maltrin feed was stopped 97 h after inoculation, backpressure and aeration lowered to respectively 0.2 bar and 4 L/min. (0.5 vvm), and co-enzyme B$_{12}$ added to a final concentration of 10 mg/L. When the culture was 122 h old, broth was harvested, centrifuged, and 0.2 L of ethanol added to 1 L of supernatant.

One L of cell-free fermentation broth was vacuum-distilled, yielding about 60 mL of a dark slurry. The slurry was centrifuged, and about 40 mL of liquid supernatant were collected. This liquid was then treated with 40 mL of ethanol in order to precipitate out residual solids, which were removed by centrifugation. A small sample of the decanted liquid was analyzed by HPLC and found to contain 1,3-propanediol: the identity of the propanediol was confirmed by GC/MS.

Applicants have deposited a recombinant *Aspergillus niger* strain TGR40-13, comprising a DNA fragment encoding dhaB(1-3), dhaBx and dhaT (ATCC 74369).

Example 23

Production of 1,3-propanediol from Maltose using Recombinant *A. niger*

*Aspergillus* fermentations are carried out in 15.5 L total volume Biolafitte fermenters, working volume initially 8 L, increasing to 11 L during the run. Aerobic conditions are insured by aeration with air at a rate of 10 L/min, at an impeller speed of 700-800 rpm and a back-pressure of 1.1 bar (aerobic conditions are defined by the % Dissolved Oxygen (100% DO defined at ambient pressure), measured with installed DO-probes; a minimal value of 35% DO was considered aerobic). The pH is maintained at 5.60 by automatic addition of 10% H$_3$PO$_4$ or 28% NH$_4$OH. Temperature is maintained at 32° C.

The following compounds are batched into the tank and sterilized at 121° C. for 30 min: 2 g/L NaH$_2$PO$_4$.H$_2$O, 17 g/L (NH$_4$)$_2$SO$_4$, 1 g/L MgSO$_4$, 2 g/L Tween 80, 45 g/L Promosoy-100 (a soy concentrate of 70% protein), 6 g/L corn steep liquor (50% solids), 10 g/L maltose, and 2 g/L MAZU DF204 (a custom-made antifoam). After sterilization, 500 gram of the 50% Maltrin 150 feed is added, together with carbenicillin and streptomycin (both up to a final concentration of 10 mg/L).

One L of a 40-48 h old *Aspergillus niger* strain transformed with dhaB1, dhaB2, dhaB3, dhaB4 and dhaT genes, growing in a shakeflask containing 10% CSL (defined in Example 22), is used to inoculate the fermenter. The culture is then allowed to grow for 30-35 h before the feed (a 50% Maltrin 150 solution, heat sterilized) is started, at a rate of 1 g/min. The culture is then run for another 5 h under O$_2$ limited conditions (% DO zero, under full aeration). After that, the Maltrin feed is stopped and when the measured glucose in the supernatant is virtually zero, the rpm is lowered to 150, the BP to 0.2, and aeration is stopped. The fermenter is flushed with an anaerobic gas-mixture (5% H$_2$, 5% CO$_2$, 90% N$_2$) at a rate of 7 L/min for 30 min. Gas inlet and outlet is then closed, BP is maintained at 0.4 bar, and co-enzyme B$_{12}$ is added to a final concentration of 5 mg/L. Throughout, broth samples are centrifuged and the supernatants are prepared for HPLC and GC analysis. 1,3-propanediol is detected in the supernatant.

Example 24

Production of 1,3-propanediol from Substrates Other Than Glycerol by *Lactobacillus reuteri* (ATCC 23272)

*Lactobacillus reuteri* (ATCC 23272) was maintained on MRS (Difco, Detroit, Mich.) plates. Colonies from a plate were used to inoculate 70 mL *Lactobacillus* MRS broth (Difco #0881-17) supplemented with 25 mM NaHCO$_3$ in a 250 mL Erlenmeyer flask. The flask was incubated in an anaerobic atmosphere (5-7% H$_2$, 2-8% CO$_2$, 85-93% N$_2$) at 32-C.

HPLC analysis of *Lactobacillus* MRS broth showed a component with the retention time of glycerol. *Lactobacillus* MRS broth was treated by alkaline boiling and analyzed for glycerol by HPLC and enzymatic assay. At most, 0.25 g/L glycerol could be detected in the initial medium; if all of this glycerol was transformed to 1,3-propanediol, 0.21 g/L propanediol could be said to have been produced from glycerol.

After 10 d of incubation, a sample from the *Lactobacillus reuteri* culture flask was removed, analyzed by HPLC and GC-MS, and compared to an initial medium sample. Correcting for the glycerol present in the medium, 1.35 g/L 1,3-propanediol was produced by *Lactobacillus reuteri* from substrates other than glycerol.

---

What is claimed is:

1. An isolated microorganism transformed with polynucleotide sequences encoding an active glycerol dehydratase enzyme, said polynucleotide sequences comprising nucleotide bases 7044-8711, 8724-9308, and 9311-9736 of SEQ ID NO:1; and at least one polynucleotide sequence encoding an active functional protein, said polynucleotide sequence selected from the group consisting of nucleotide bases 1-399, 983-2107, 2209-4134, 5017-6180, and 9749-11572 of SEQ ID NO:1; said isolated microorganism being capable of producing 1,3-propanediol in the presence of a carbon substrate other than glycerol and/or dihydroxyacetone.

2. A recombinant *Pseudomonas* sp. comprising a DNA fragment encoding glycerol dehydratase subunit B1 (dhaB1), glycerol dehydratase subunit B2 (dhaB2), and glycerol dehydratase subunit B3 (dhaB3) and 1,3-propanediol oxidoreductase (dhaT) and designated by ATCC Accession No. 55760.

3. A recombinant *Pichia pastoris* comprising a DNA fragment encoding dhaB1, dhaB2, and dhaB3 and dhaT and designated by ATCC Accession No. 74363.

4. A recombinant *Saccharomyces cerevisiae* strain pMCK1/10/17 (MH) #A, comprising a DNA fragment encoding dhaB1, dhaB2, and dhaB3, and dhaT and designated by ATCC Accession No. 74370.

5. A recombinant *Bacillus licheniformis* strain BG188/pM26 (Clone #8), comprising a DNA fragment encoding dhaB1, dhaB2, and dhaB3, and designated by ATCC Accession No. 98051.

6. A recombinant *Bacillus subtilis* strain BG2864/pM27 (Clone #1), comprising a DNA fragment encoding dhaB1, dhaB2, dhaB3, and dhaT and designated by ATCC Accession No. 98050.

7. A recombinant *Streptomyces lividans* strain SL 14·2, comprising a DNA fragment encoding dhaB1, dhaB2, and dhaB3 and dhaT and designated by ATCC Accession No. 98052.

8. A recombinant *Aspergillus niger* strain TGR40-13, comprising a DNA fragment encoding dhaB1, dhaB2, dhaB3, and dhaT and designated by ATCC Accession No. 74369.

* * * * *

SEQUENCE LISTING (1) GENERAL INFORMATION:

(iii) NUMBER OF SEQUENCES: 46

(2) INFORMATION FOR SEQ ID NO: 1:

(i) SEQUENCE CHARACTERISTICS:
        (A) LENGTH: 12145 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

```
GTCGACCACC ACGGTGGTGA CTTTAATGCC GCTCTCATGC AGCAGCTCGG TGGCGGTCTC      60
AAAATTCAGG ATGTCGCCGG TATAGTTTTT GATAATCAGC AAGACGCCTT CGCCGCCGT      120
AATTTGCATC GCGCATTCAA ACATTTTGTC CGGCGTCGGC GAGGTGAATA TTTCCCCCG      180
ACAGGCGCCG GAGAGCATGC CCTGGCCGAT ATAGCCGCAG TGCATCGGTT CATGTCCGC      240
GCCGCCGCCG GAGAGCAGGG CCACCTTGCC AGCCACCGGC GCGTCGGTGC GGGTCACAT      300
CAGCGGGTCC TGATGCAGGG TCAGCTGCGG ATGGGCTTTA GCCAGCCCCT GTAATTGTT      360
ATTCAGTACA TCTTCAACAC GGTTAATCAG CTTTTTCATT ATTCAGTGCT CCGTTGGAG      420
AGGTTCGATG CCGCCTCTCT GCTGGCGGAG GCGGTCATCG CGTAGGGGTA TCGTCTGAC      480
GTGGAGCGTG CCTGGCGATA TGATGATTCT GGCTGAGCGG ACGAAAAAAA GAATGCCCC      540
ACGATCGGGT TTCATTACGA AACATTGCTT CCTGATTTTG TTTCTTTATG GAACGTTTT      600
GCTGAGGATA TGGTGAAAAT GCGAGCTGGC GCGCTTTTTT TCTTCTGCCA TAAGCGGCG      660
TCAGGATAGC CGGCGAAGCG GGTGGGAAAA AATTTTTTGC TGATTTTCTG CCGACTGCG      720
GAGAAAAGGC GGTCAAACAC GGAGGATTGT AAGGGCATTA TGCGGCAAAG GAGCGGATC      780
GGATCGCAAT CCTGACAGAG ACTAGGGTTT TTTGTTCCAA TATGGAACGT AAAAAATTA      840
CCTGTGTTTC ATATCAGAAC AAAAAGGCGA AAGATTTTTT TGTTCCCTGC CGGCCCTAC      900
GTGATCGCAC TGCTCCGGTA CGCTCCGTTC AGGCCGCGCT TCACTGGCCG GCGCGGATA      960
CGCCAGGGCT CATCATGTCT ACATGCGCAC TTATTTGAGG GTGAAAGGAA TGCTAAAA     1020
TATTCAATCT CCAGCCAAAT ATCTTCAGGG TCCTGATGCT GCTGTTCTGT TCGGTCAA     1080
TGCCAAAAAC CTGGCGGAGA GCTTCTTCGT CATCGCTGAC GATTTCGTAA TGAAGCTG     1140
GGGAGAGAAA GTGGTGAATG GCCTGCAGAG CCACGATATT CGCTGCCATG CGGAACGG     1200
TAACGGCGAA TGCAGCCATG CGGAAATCAA CCGTCTGATG GCGATTTTGC AAAAACAG     1260
```

-continued

| | |
|---|---|
| CTGCCGCGGC GTGGTCGGGA TCGGCGGTGG TAAAACCCTC GATACCGCGA AGGCGATC | 1320 |
| TTACTACCAG AAGCTGCCGG TGGTGGTGAT CCCGACCATC GCCTCGACCG ATGCGCCA | 1380 |
| CAGCGCGCTG TCGGTGATCT ACACCGAAGC GGGCGAGTTT GAAGAGTATC TGATCTAT | 1440 |
| GAAAAACCCG GATATGGTGG TGATGGACAC GGCGATTATC GCCAAAGCGC CGGTACGC | 1500 |
| GCTGGTCTCC GGCATGGGCG ATGCGCTCTC CACCTGGTTC GAGGCCAAAG CTTGCTAC | 1560 |
| TGCGCGCGCC ACCAGCATGG CCGGAGGACA GTCCACCGAG GCGGCGCTGA GCCTCGCC | 1620 |
| CCTGTGCTAT GATACGCTGC TGGCGGAGGG CGAAAAGGCC CGTCTGGCGG CGCAGGCC | 1680 |
| GGTAGTGACC GAAGCGCTGG AGCGCATCAT CGAGGCGAAC ACTTACCTCA GCGGCATT | 1740 |
| CTTTGAAAGC AGTGGCCTGG CCGCTGCCCA TGCAATCCAC AACGGTTTCA CCATTCTT | 1800 |
| AGAGTGCCAT CACCTGTATC ACGGTGAGAA AGTGGCCTTC GGTACCCTGG CGCAGCTG | 1860 |
| GCTGCAGAAC AGCCCGATGG ACGAGATTGA AACGGTGCAG GGCTTCTGCC AGCGCGTC | 1920 |
| CCTGCCGGTG ACGCTCGCGC AGATGGGCGT CAAAGAGGGG ATCGACGAGA AAATCGCC | 1980 |
| GGTGGCGAAA GCTACCTGCG CGGAAGGGGA AACCATCCAT AATATGCCGT TGCGGTG | 2040 |
| CCCGGAGAGC GTCCATGCCG CTATCCTCAC CGCCGATCTG TTAGGCCAGC AGTGGCTG | 2100 |
| GCGTTAATTC GCGGTGGCTA AACCGCTGGC CCAGGTCAGC GGTTTTTCTT TCTCCCCT | 2160 |
| GGCAGTCGCT GCCGGAGGGG TTCTCTATGG TACAACGCGG AAAAGGATAT GACTGTTC | 2220 |
| ACTCAGGATA CCGGGAAGGC GGTCTCTTCC GTCATTGCCC AGTCATGGCA CCGCTGCA | 2280 |
| AAGTTTATGC AGCGCGAAAC CTGGCAAACG CCGCACCAGG CCCAGGGCCT GACCTTCG | 2340 |
| TCCATCTGTC GGCGTAAAAC CGCGCTGCTC ACCATCGGCC AGGCGGCGCT GGAAGACG | 2400 |
| TGGGAGTTTA TGGACGGCCG CCCCTGCGCG CTGTTTATTC TTGATGAGTC CGCCTGCA | 2460 |
| CTGAGCCGTT GCGGCGAGCC GCAAACCCTG GCCCAGCTGG CTGCCCTGGG ATTTCGCG | 2520 |
| GGCAGCTATT GTGCGGAGAG CATTATCGGC ACCTGCGCGC TGTCGCTGGC CGCGATGC | 2580 |
| GGCCAGCCGA TCAACACCGC CGGCGATCGG CATTTTAAGC AGGCGCTACA GCCATGGA | 2640 |
| TTTTGCTCGA CGCCGGTGTT TGATAACCAC GGGCGGCTGT TCGGCTCTAT CTCGCTTT | 2700 |
| TGTCTGGTCG AGCACCAGTC CAGCGCCGAC CTCTCCCTGA CGCTGGCCAT CGCCCGCG | 2760 |
| GTGGGTAACT CCCTGCTTAC CGACAGCCTG CTGGCGGAAT CCAACCGTCA CCTCAATC | 2820 |
| ATGTACGGCC TGCTGGAGAG CATGGACGAT GGGGTGATGG CGTGGAACGA ACAGGGCG | 2880 |
| CTGCAGTTTC TCAATGTTCA GGCGGCGAGA CTGCTGCATC TTGATGCTCA GGCCAGCC | 2940 |
| GGGAAAAATA TCGCCGATCT GGTGACCCTC CCGGCGCTGC TGCGCCGCGC CATCAAAC | 3000 |
| GCCCGCGGCC TGAATCACGT CGAAGTCACC TTTGAAAGTC AGCATCAGTT TGTCGATG | 3060 |
| GTGATCACCT TAAAACCGAT TGTCGAGGCG CAAGGCAACA GTTTTATTCT GCTGCTGC | 3120 |
| CCGGTGGAGC AGATGCGGCA GCTGATGACC AGCCAGCTCG GTAAAGTCAG CCACACCT | 3180 |
| GAGCAGATGT CTGCCGACGA TCCGGAAACC CGACGCCTGA TCCACTTTGG CCGCCAGG | 3240 |
| GCGCGCGGCG GCTTCCCGGT GCTACTGTGC GGCGAAGAGG GGGTCGGGAA AGAGCTGC | 3300 |
| AGCCAGGCTA TTCACAATGA AAGCGAACGG GCGGGCGGCC CCTACATCTC CGTCAACT | 3360 |
| CAGCTATATG CCGACAGCGT GCTGGGCCAG GACTTTATGG GCAGCGCCCC TACCGACG | 3420 |
| GAAAATGGTC GCCTGAGCCG CCTTGAGCTG GCCAACGGCG GCACCCTGTT TCTGGAAA | 3480 |
| ATCGAGTATC TGGCGCCGGA GCTGCAGTCG GCTCTGCTGC AGGTGATTAA GCAGGGCG | 3540 |
| CTCACCCGCC TCGACGCCCG GCGCCTGATC CCGGTGGATG TGAAGGTGAT TGCCACCA | 3600 |
| ACCGTCGATC TGGCCAATCT GGTGGAACAG AACCGCTTTA GCCGCCAGCT GTACTATG | 3660 |

```
CTGCACTCCT TTGAGATCGT CATCCCGCCG CTGCGCGCCC GACGCAACAG TATTCCGT      3720
CTGGTGCATA ACCGGTTGAA GAGCCTGGAG AAGCGTTTCT CTTCGCGACT GAAAGTGG      3780
GATGACGCGC TGGCACAGCT GGTGGCCTAC TCGTGGCCGG GGAATGATTT TGAGCTCA      3840
AGCGTCATTG AGAATATCGC CATCAGCAGC GACAACGGCC ACATTCGCCT GAGTAATC      3900
CCGGAATATC TCTTTTCCGA GCGGCCGGGC GGGGATAGCG CGTCATCGCT GCTGCCGG      3960
AGCCTGACTT TTAGCGCCAT CGAAAAGGAA GCTATTATTC ACGCCGCCCG GGTGACCA      4020
GGGCGGGTGC AGGAGATGTC GCAGCTGCTC AATATCGGCC GCACCACCCT GTGGCGCA      4080
ATGAAGCAGT ACGATATTGA CGCCAGCCAG TTCAAGCGCA AGCATCAGGC CTAGTCTC      4140
CGATTCGCGC CATGGAGAAC AGGGCATCCG ACAGGCGATT GCTGTAGCGT TTGAGCGC      4200
CGCGCAGCGG ATGCGCGCGG TCCATGGCCG TCAGCAGGCG TTCGAGCCGA CGGGACTG      4260
TGCGCGCCAC GTGCAGCTGG GCAGAGGCGA GATTCCTCCC CGGGATCACG AACTGTTT      4320
ACGGGCCGCT CTCGGCCATA TTGCGGTCGA TAAGCCGCTC CAGGGCGGTG ATCTCCTC      4380
CGCCGATCGT CTGGCTCAGG CGGGTCAGGC CCCGCGCATC GCTGGCCAGT TCAGCCCC      4440
GCACGAACAG CGTCTGCTGA ATATGGTGCA GGCTTTCCCG CAGCCCGGCG TCGCGGGT      4500
TGGCGTAGCA GACGCCCAGC TGGGATATCA GTTCATCGAC GGTGCCGTAG CCTCGAC       4560
GAATATGGTC TTTCTCGATG CGGCTGCCGC CGTACAGGGC GGTGGTGCCT TTATCCCC      4620
TGCGGGTATA GATACGATAC ATTCAGTTTC TCTCACTTAA CGGCAGGACT TTAACCAG      4680
GCCCGGCGTT GGCGCCGAGC GTACGCAGTT GATCGTCGCT ATCGGTGACG TGTCCGGT      4740
CCAGCGGCGC GTCCGCCGGC AGCTGGGCAT GAGTGAGGGC TATCTCGCCG GACGCGCT      4800
GCCCGATACC CACCCGCAGG GGCGAGCTTC TGGCCGCCAG GGCGCCCAGC GCAGCGGC      4860
CACCGCCTCC GTCATAGGTT ATGGTCTGGC AGGGGACCCC CTGCTCCTCC AGCCCCCA      4920
ACAGCTCATT GATGGCGCCG GCATGGTGCC CGCGCGGATC GTAAAACAGG CGTACGCC      4980
GCGGTGAAAG CGACATGACG GTCCCCTCGT TAACACTCAG AATGCCTGGC GGAAAATC      5040
GGCAATCTCC TGCTCGTTGC CTTTACGCGG GTTCGAGAAC GCATTGCCGT CTTTTAGA      5100
CATCTCCGCC ATGTAGGGGA AGTCGGCCTC TTTTACCCCC AGATCGCGCA GATGCTGC      5160
AATACCGATA TCCATCGACA GACGCGTGAT AGCGGCGATG GCTTTTTCCG CCGCGTCG      5220
AGTGGACAGT CCGGTGATAT TTTCGCCCAT CAGTTCAGCG ATATCGGCGA ATTTCTCC      5280
GTTGGCGATC AGGTTGTAGC GCGCCACATG CGGCAGCAGG ACAGCGTTGG CCACGCCG      5340
CGGCATGTCG TACAGGCCGC CCAGCTGGTG CGCCATGGCG TGCACGTAGC CGAGGTTG      5400
GTTATTGAAA GCCATCCCGG CCAGCAGAGA AGCATAGGCC ATGTTTTCCC GCGCCTGC      5460
ATTGCTGCCG AGGGCCACGG CCTGGCGCAG GTTGCGGGCG ATGAGGCGGA TCGCCTGC      5520
GGCGGCGGCG TCCGTCACCG GGTTAGCGTC TTTGGAGATA TAGGCCTCTA CGGCGTGG      5580
CAGGGCATCC ATCCCGGTCG CCGCGGTCAG GGCGGCCGGT TTACCGATCA TCAGCAGT      5640
ATCGTTGATA GAGACCGACG GCAGTTTGCG CCAGCTGACG ATCACAAACT TCACTTTG      5700
TTCGGTGTTG GTCAGGACGC AGTGGCGGGT GACCTCGCTG GCGGTGCCGG CGGTGGTA      5760
GACCGCGACG ATAGGCGGCA GCGGGTTGGT CAGGGTCTCG ATTCCGGCAT ACTGGTAC      5820
ATCGCCCTCA TGGGTGGCGG CGATGCCGAT GCCTTTGCCG CAATCGTGCG GGCTGCCG      5880
GCCCACGGTG ACGATGATGT CGCACTGTTC GCGGCGAAAC ACGGCGAGGC CGTCGCGC      5940
GTTGGTGTCT TTCGGGTTCG GCTCGACGCC GTCAAAGATC GCCACCTCGA TCCCGGCC      6000
```

| | |
|---|---|
| CCGCAGATAA TGCAGGGTTT TGTCCACCGC GCCATCTTTA ATTGCCCGCA GGCCTTTG | 6060 |
| GGTGACCAGC AGGGCTTTTT TCCCCCCCAG CAGCTGGCAG CGTTCGCCGA CTACGGAA | 6120 |
| GGCGTTGGGG CCAAAAAAGT TAACGTTTGG CACCAGATAA TCAAACATAC GATAGCTC | 6180 |
| AATATACCTT CTCGCTTCAG GTTATAATGC GGAAAAACAA TCCAGGGCGC ACTGGGCT | 6240 |
| TAATTGATCC TGCTCGACCG TACCGCCGCT AACGCCGACG GCGCCAATTA CCTGCTCA | 6300 |
| AAAAATAACT GGCAGGCCGC CGCCAAAAAT AATAATTCGC TGTTGGTTGG TTAGCTGC | 6360 |
| ACCGTACAGA GATTGTCCTG GCTGGACCGC TGACGTAATT TCATGGGTAC CTTGCTTC | 6420 |
| GCTGCAGGCG CTCCAGGCTT TATTCAGGGA AATATCGCAG CTGGAGACGA AGGCCTCG | 6480 |
| CATCCGCTGG ATAAGCAGCG TGTTGCCTCC GCGGTCAACT ACGGAAAACA CCACCGCC | 6540 |
| GTTGATCTCA GTGGCTTTTT TTTCCACCGC CGCCGCCATT TGCTGGGCGG CGGCCAGG | 6600 |
| GATTGTCTGA ACTTGTTGGC TCTTGTTCAT CATTCTCTCC CGCACCAGGA TAACGCTG | 6660 |
| GCGAATAGTC AGTAGGGGGC GATAGTAAAA AACTATTACC ATTCGGTTGG CTTGCTTT | 6720 |
| TTTTGTCAGC GTTATTTTGT CGCCCGCCAT GATTTAGTCA ATAGGGTTAA AATAGCGT | 6780 |
| GAAAAACGTA ATTAAGGGCG TTTTTTATTA ATTGATTTAT ATCATTGCGG GCGATCAC | 6840 |
| TTTTTATTTT TGCCGCCGGA GTAAAGTTTC ATAGTGAAAC TGTCGGTAGA TTTCGTGT | 6900 |
| CAAATTGAAA CGAAATTAAA TTTATTTTTT TCACCACTGG CTCATTTAAA GTTCCGCT | 6960 |
| TGCCGGTAAT GGCCGGGCGG CAACGACGCT GGCCCGGCGT ATTCGCTACC GTCTGCGG | 7020 |
| TTCACCTTTT GAGCCGATGA ACAATGAAAA GATCAAAACG ATTTGCAGTA CTGGCCCA | 7080 |
| GCCCCGTCAA TCAGGACGGG CTGATTGGCG AGTGGCCTGA AGAGGGGCTG ATCGCCAT | 7140 |
| ACAGCCCCTT TGACCCGGTC TCTTCAGTAA AAGTGGACAA CGGTCTGATC GTCGAACT | 7200 |
| ACGGCAAACG CCGGGACCAG TTTGACATGA TCGACCGATT TATCGCCGAT TACGCGAT | 7260 |
| ACGTTGAGCG CACAGAGCAG GCAATGCGCC TGGAGGCGGT GGAAATAGCC CGTATGCT | 7320 |
| TGGATATTCA CGTCAGCCGG GAGGAGATCA TTGCCATCAC TACCGCCATC ACGCCGGC | 7380 |
| AAGCGGTCGA GGTGATGGCG CAGATGAACG TGGTGGAGAT GATGATGGCG CTGCAGAA | 7440 |
| TGCGTGCCCG CCGGACCCCC TCCAACCAGT GCCACGTCAC CAATCTCAAA GATAATCC | 7500 |
| TGCAGATTGC CGCTGACGCC GCCGAGGCCG GGATCCGCGG CTTCTCAGAA CAGGAGAC | 7560 |
| CGGTCGGTAT CGCGCGCTAC GCGCCGTTTA ACGCCCTGGC GCTGTTGGTC GGTTCGCA | 7620 |
| GCGGCCGCCC CGGCGTGTTG ACGCAGTGCT CGGTGGAAGA GGCCACCGAG CTGGAGCT | 7680 |
| GCATGCGTGG CTTAACCAGC TACGCCGAGA CGGTGTCGGT CTACGGCACC GAAGCGGT | 7740 |
| TTACCGACGG CGATGATACG CCGTGGTCAA AGGCGTTCCT CGCCTCGGCC TACGCCTC | 7800 |
| GCGGGTTGAA AATGCGCTAC ACCTCCGGCA CCGGATCCGA AGCGCTGATG GGCTATTC | 7860 |
| AGAGCAAGTC GATGCTCTAC CTCGAATCGC GCTGCATCTT CATTACTAAA GGCGCCGG | 7920 |
| TTCAGGGACT GCAAAACGGC GCGGTGAGCT GTATCGGCAT GACCGGCGCT GTGCCGTC | 7980 |
| GCATTCGGGC GGTGCTGGCG GAAAACCTGA TCGCCTCTAT GCTCGACCTC GAAGTGGC | 8040 |
| CCGCCAACGA CCAGACTTTC TCCCACTCGG ATATTCGCCG CACCGCGCGC ACCCTGAT | 8100 |
| AGATGCTGCC GGGCACCGAC TTTATTTTCT CCGGCTACAG CGCGGTGCCG AACTACGA | 8160 |
| ACATGTTCGC CGGCTCGAAC TTCGATGCGG AAGATTTTGA TGATTACAAC ATCCTGCA | 8220 |
| GTGACCTGAT GGTTGACGGC GGCCTGCGTC CGGTGACCGA GGCGGAAACC ATTGCCAT | 8280 |
| GCCAGAAAGC GGCGCGGGCG ATCCAGGCGG TTTTCCGCGA GCTGGGGCTG CCGCCAAT | 8340 |
| CCGACGAGGA GGTGGAGGCC GCCACCTACG CGCACGGCAG CAACGAGATG CCGCCGCG | 8400 |

```
ACGTGGTGGA GGATCTGAGT GCGGTGGAAG AGATGATGAA GCGCAACATC ACCGGCCT      8460
ATATTGTCGG CGCGCTGAGC CGCAGCGGCT TTGAGGATAT CGCCAGCAAT ATTCTCAA      8520
TGCTGCGCCA GCGGGTCACC GGCGATTACC TGCAGACCTC GGCCATTCTC GATCGGCA      8580
TCGAGGTGGT GAGTGCGGTC AACGACATCA ATGACTATCA GGGGCCGGGC ACCGGCTA      8640
GCATCTCTGC CGAACGCTGG GCGGAGATCA AAAATATTCC GGGCGTGGTT CAGCCCGA      8700
CCATTGAATA AGGCGGTATT CCTGTGCAAC AGACAACCCA AATTCAGCCC TCTTTTAC      8760
TGAAAACCCG CGAGGGCGGG GTAGCTTCTG CCGATGAACG CGCCGATGAA GTGGTGAT      8820
GCGTCGGCCC TGCCTTCGAT AAACACCAGC ATCACACTCT GATCGATATG CCCCATGG      8880
CGATCCTCAA AGAGCTGATT GCCGGGGTGG AAGAAGAGGG GCTTCACGCC CGGGTGGT      8940
GCATTCTGCG CACGTCCGAC GTCTCCTTTA TGGCCTGGGA TGCGGCCAAC CTGAGCGG      9000
CGGGGATCGG CATCGGTATC CAGTCGAAGG GGACCACGGT CATCCATCAG CGCGATCT      9060
TGCCGCTCAG CAACCTGGAG CTGTTCTCCC AGGCGCCGCT GCTGACGCTG GAGACCTA      9120
GGCAGATTGG CAAAAACGCT GCGCGCTATG CGCGCAAAGA GTCACCTTCG CCGGTGCC      9180
TGGTGAACGA TCAGATGGTG CGGCCGAAAT TTATGGCCAA AGCCGCGCTA TTTCATAT      9240
AAGAGACCAA ACATGTGGTG CAGGACGCCG AGCCCGTCAC CCTGCACATC GACTTAGT      9300
GGGAGTGACC ATGAGCGAGA AAACCATGCG CGTGCAGGAT TATCCGTTAG CCACCCGC      9360
CCCGGAGCAT ATCCTGACGC CTACCGGCAA ACCATTGACC GATATTACCC TCGAGAAG      9420
GCTCTCTGGC GAGGTGGGCC CGCAGGATGT GCGGATCTCC CGCCAGACCC TTGAGTAC      9480
GGCGCAGATT GCCGAGCAGA TGCAGCGCCA TGCGGTGGCG CGCAATTTCC GCCGCGCG      9540
GGAGCTTATC GCCATTCCTG ACGAGCGCAT TCTGGCTATC TATAACGCGC TGCGCCCG      9600
CCGCTCCTCG CAGGCGGAGC TGCTGGCGAT CGCCGACGAG CTGGAGCACA CCTGGCAT      9660
GACAGTGAAT GCCGCCTTTG TCCGGGAGTC GGCGGAAGTG TATCAGCAGC GGCATAAG      9720
GCGTAAAGGA AGCTAAGCGG AGGTCAGCAT GCCGTTAATA GCCGGGATTG ATATCGGC      9780
CGCCACCACC GAGGTGGCGC TGGCGTCCGA CTACCCGCAG GCGAGGGCGT TTGTTGCC      9840
CGGGATCGTC GCGACGACGG GCATGAAAGG GACGCGGGAC AATATCGCCG GACCCTC       9900
CGCGCTGGAG CAGGCCCTGG CGAAAACACC GTGGTCGATG AGCGATGTCT CTCGCATC      9960
TCTTAACGAA GCCGCGCCGG TGATTGGCGA TGTGGCGATG GAGACCATCA CCGAGAC      10020
TATCACCGAA TCGACCATGA TCGGTCATAA CCCGCAGACG CCGGGCGGGG TGGGCGT      10080
CGTGGGGACG ACTATCGCCC TCGGGCGGCT GGCGACGCTG CCGGCGGCGC AGTATGC      10140
GGGGTGGATC GTACTGATTG ACGACGCCGT CGATTTCCTT GACGCCGTGT GGTGGCT      10200
TGAGGCGCTC GACCGGGGGA TCAACGTGGT GGCGGCGATC CTCAAAAAGG ACGACGG      10260
GCTGGTGAAC AACCGCCTGC GTAAAACCCT GCCGGTGGTG GATGAAGTGA CGCTGCT      10320
GCAGGTCCCC GAGGGGGTAA TGGCGGCGGT GGAAGTGGCC GCGCCGGGCC AGGTGGT      10380
GATCCTGTCG AATCCCTACG GGATCGCCAC CTTCTTCGGG CTAAGCCCGG AAGAGAC      10440
GGCCATCGTC CCCATCGCCC GCGCCCTGAT TGGCAACCGT TCCGCGGTGG TGCTCAA      10500
CCCGCAGGGG GATGTGCAGT CGCGGGTGAT CCCGGCGGGC AACCTCTACA TTAGCGG      10560
AAAGCGCCGC GGAGAGGCCG ATGTCGCCGA GGGCGCGGAA GCCATCATGC AGGCGAT      10620
CGCCTGCGCT CCGGTACGCG ACATCCGCGG CGAACCGGGC ACCCACGCCG GCGGCAT      10680
TGAGCGGGTG CGCAAGGTAA TGGCGTCCCT GACCGGCCAT GAGATGAGCG CGATATA      10740
```

```
CCAGGATCTG CTGGCGGTGG ATACGTTTAT TCCGCGCAAG GTGCAGGGCG GGATGGC        10800

CGAGTGCGCC ATGGAGAATG CCGTCGGGAT GGCGGCGATG GTGAAAGCGG ATCGTCT        10860

AATGCAGGTT ATCGCCCGCG AACTGAGCGC CCGACTGCAG ACCGAGGTGG TGGTGGG        10920

CGTGGAGGCC AACATGGCCA TCGCCGGGGC GTTAACCACT CCCGGCTGTG CGGCGCC        10980

GGCGATCCTC GACCTCGGCG CCGGCTCGAC GGATGCGGCG ATCGTCAACG CGGAGGG        11040

GATAACGGCG GTCCATCTCG CCGGGGCGGG GAATATGGTC AGCCTGTTGA TTAAAAC        11100

GCTGGGCCTC GAGGATCTTT CGCTGGCGGA AGCGATAAAA AAATACCCGC TGGCCAA        11160

GGAAAGCCTG TTCAGTATTC GTCACGAGAA TGGCGCGGTG GAGTTCTTTC GGGAAGC        11220

CAGCCCGGCG GTGTTCGCCA AGTGGTGTA  CATCAAGGAG GGCGAACTGG TGCCGAT        11280

TAACGCCAGC CCGCTGGAAA AAATTCGTCT CGTGCGCCGG CAGGCGAAAG AGAAAGT        11340

TGTCACCAAC TGCCTGCGCG CGCTGCGCCA GGTCTCACCC GGCGGTTCCA TTCGCGA        11400

CGCCTTTGTG GTGCTGGTGG GCGGCTCATC GCTGGACTTT GAGATCCCGC AGCTTAT        11460

GGAAGCCTTG TCGCACTATG GCGTGGTCGC CGGGCAGGGC AATATTCGGG GAACAGA        11520

GCCGCGCAAT GCGGTCGCCA CCGGGCTGCT ACTGGCCGGT CAGGCGAATT AAACGGG        11580

TCGCGCCAGC CTCTCTCTTT AACGTGCTAT TTCAGGATGC CGATAATGAA CCAGACT        11640

ACCTTAACCG GGCAGTGCGT GGCCGAGTTT CTTGGCACCG GATTGCTCAT TTTCTTC        11700

GCGGGCTGCG TCGCTGCGCT GCGGGTCGCC GGGGCCAGCT TTGGTCAGTG GGAGATC        11760

ATTATCTGGG GCCTTGGCGT CGCCATGGCC ATCTACCTGA CGGCCGGTGT CTCCGGC        11820

CACCTAAATC CGGCGGTGAC CATTGCCCTG TGGCTGTTCG CCTGTTTTGA ACGCCGC        11880

GTGCTGCCGT TTATTGTTGC CCAGACGGCC GGGGCCTTCT GCGCCGCCGC GCTGGTG        11940

GGGCTCTATC GCCAGCTGTT TCTCGATCTT GAACAGAGTC AGCATATCGT GCGCGGC        12000

GCCGCCAGTC TTAACCTGGC CGGGGTCTTT TCCACGTACC CGCATCCACA TATCACT        12060

ATACAAGCGT TGCCGTGGA  GACCACCATC ACGGCAATCC TGATGGCGAT GATCATG        12120

CTGACCGACG ACGGCAACGG AATTC                                          12145

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GGGAATTCAT GAAAAGATCA AAACGATTTG                                     30

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

GCGAATTCTT ATTCAATGGT GTCGGGCTG                                      29
```

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GCGAATTCAT GCAACAGACA ACCCAAATTC                                            30

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GCGAATTCAC TCCCTTACTA AGTCG                                                 25

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GCGAATTCAT GAGCTATCGT ATGTTTG                                               27

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GCGAATTCAG AATGCCTGGC GGAAAATC                                              28

(2) INFORMATION FOR SEQ ID NO: 8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GGGAATTCAT GAGCGAGAAA ACCATGCG                                              28

(2) INFORMATION FOR SEQ ID NO: 9:

(i) SEQUENCE CHARACTERISTICS:
        (A) LENGTH: 27 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 9:

GCGAATTCTT AGCTTCCTTT ACGCAGC                                          27

(2) INFORMATION FOR SEQ ID NO: 10:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 10:

AGCTTAGGAG TCTAGAATAT TGAGCTCGAA TTCCCGGGCA TGCGGTACCG GATCCAGAAA      60

AAAGCCCGCA CCTGACAGTG CGGGCTTTTT TTTT                                  94

(2) INFORMATION FOR SEQ ID NO: 11:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 11:

GGCCAAGCTT AAGGAGGTTA ATTAAATGAA AAG                                   33

(2) INFORMATION FOR SEQ ID NO: 12:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 12:

GCTCTAGATT ATTCAATGGT GTCGGG                                           26

(2) INFORMATION FOR SEQ ID NO: 13:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 13:

GCGCCGTCTA GAATTATGAG CTATCGTATG TTTGATTATC TG                         42

(2) INFORMATION FOR SEQ ID NO: 14:

(i) SEQUENCE CHARACTERISTICS:
            (A) LENGTH: 36 base pairs
            (B) TYPE: nucleic acid
            (C) STRANDEDNESS: single
```

(D) TOPOLOGY: linear (ii) MOLECULE TYPE: DNA (genomic)

(xi) SEQUENCE DESCRIPTION: SEQ ID NO: 14:

TCTGATACGG GATCCTCAGA ATGCCTGGCG GAAAAT                                    36

(2) INFORMATION FOR SEQ ID NO: 15:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CGATCTGTGC TGTTTGCCAC GGTATGCAGC ACCAGCGCGA GATTATGGGC TCGCACGCTC          60

GACTGTCGGA CGGGGGCACT GGAACGAGAA GTCAGGCGAG CCGTCACGCC CTTGACAAT         120

CCACATCCTG AGCAAATAAT TCAACCACTA AACAAATCAA CCGCGTTTCC CGGAGGTAA         180

C                                                                       181

(2) INFORMATION FOR SEQ ID NO: 16:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

CGATCTGTGC TGTTTGCCAC GGTATGCAGC ACCAGCGCGA GATTATGGGC TCGCACGCTC          60

GACTGTCGGA CGGGGGCACT GGAACATGCC ACATCCTGAG CAAATAATTC AACCACTAA         120

CAAATCAACC GCGTTTCCCG GAGGTAACC                                          149

(2) INFORMATION FOR SEQ ID NO: 17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GGAATTCACT AGTCGATCTG TGCTGTTTGC CAC                                      33

(2) INFORMATION FOR SEQ ID NO: 18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GGGGAAGCTT GGTTACCTCC GGGAAACGCG GTT                                      33

-continued (2) INFORMATION FOR SEQ ID NO: 19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

TCGACCACAA GGAGGA                                              16

(2) INFORMATION FOR SEQ ID NO: 20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CTAGTCCTCC TTGTGG                                              16

(2) INFORMATION FOR SEQ ID NO: 21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

ACTGGCCGTC GTTTTACTCG AGTCGTGACT GGGAAAACCC TGGCG                45

(2) INFORMATION FOR SEQ ID NO: 22:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

AATTCAAAGG AGGT                                                  14

(2) INFORMATION FOR SEQ ID NO: 23:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

CTAGACCTCC TTTG                                                  14

(2) INFORMATION FOR SEQ ID NO: 24:

(i) SEQUENCE CHARACTERISTICS:
        (A) LENGTH: 19 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 24:

AGCTTGTCGA CCATGAAAA                                                        19

(2) INFORMATION FOR SEQ ID NO: 25:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 25:

GATCTTTTCA TGGTCGACA                                                        19

(2) INFORMATION FOR SEQ ID NO: 26:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 26:

TCGACCAGGA GGA                                                              13

(2) INFORMATION FOR SEQ ID NO: 27:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 27:

CTAGTCCTCC TGG                                                              13

(2) INFORMATION FOR SEQ ID NO: 28:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 28:

TCGACGAATT CAGGAGGA                                                         18

(2) INFORMATION FOR SEQ ID NO: 29:

(i) SEQUENCE CHARACTERISTICS:
            (A) LENGTH: 18 base pairs
            (B) TYPE: nucleic acid
            (C) STRANDEDNESS: single
            (D) TOPOLOGY: linear
```

(ii) MOLECULE TYPE: DNA (genomic)

(xi) SEQUENCE DESCRIPTION: SEQ ID NO: 29:

CTAGTCCTCC TGAATTCG                                                      18

(2) INFORMATION FOR SEQ ID NO: 30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

ATGTACAAGA TCCTGATCGC CGA                                                23

(2) INFORMATION FOR SEQ ID NO: 31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

TCAGCGGCGC AGGTAGGCGG CG                                                 22

(2) INFORMATION FOR SEQ ID NO: 32:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

ATGACCAAGG GCCGGATCCG TCGACCTGCA G                                       31

(2) INFORMATION FOR SEQ ID NO: 33:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

CTACCCTTGG CCCCGGATCC GTCGACCTGC AG                                      32

(2) INFORMATION FOR SEQ ID NO: 34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

```
CACGGCCTGG CGCAGGTTGC GGG                                            23

(2) INFORMATION FOR SEQ ID NO: 35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

GGCAGCCCGC ACGATTGCGG C                                              21

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

GCGGAAAACC GCCTGGATCG C                                              21

(2) INFORMATION FOR SEQ ID NO: 37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

GGGTTCAGGG ACTGCAAAAC G                                              21

(2) INFORMATION FOR SEQ ID NO: 38:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

GGAATTCAGA TCTCAGCAAT GAAAGATCA AAACG                                35

(2) INFORMATION FOR SEQ ID NO: 39:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

GGAATTCAGA TCTCAGCAAT GCAACAGACA ACCC                                34

(2) INFORMATION FOR SEQ ID NO: 40:
```

```
    (i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

GCTCTAGATC ACTCCCCTTA CTAAGTCG                                              28

(2) INFORMATION FOR SEQ ID NO: 41:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

GGAATTCAGA TCTCAGCAAT GAGCGAGAAA ACCATGC                                    37

(2) INFORMATION FOR SEQ ID NO: 42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

GCTCTAGATT AGCTTCCTTT ACGCAGC                                               27

(2) INFORMATION FOR SEQ ID NO: 43:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

GGAATTCAGA TCTCAGCAAT GAGCTATCGT ATGTTTGA                                   38

(2) INFORMATION FOR SEQ ID NO: 44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

GCTCTAGATC AGAATGCCTG GCGG                                                  24

(2) INFORMATION FOR SEQ ID NO: 45:

(i) SEQUENCE CHARACTERISTICS:
        (A) LENGTH: 35 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO: 45:

GGAATTCAGA TCTAGCAATG CCGTTAATAG CCGGG                          35

(2) INFORMATION FOR SEQ ID NO: 46:

(i) SEQUENCE CHARACTERISTICS:
        (A) LENGTH: 26 base pairs
        (B) TYPE: nucleic acid
        (C) STRANDEDNESS: <Unknown>
        (D) TOPOLOGY: linear (ii) MOLECULE TYPE: DNA (genomic)

(xi) SEQUENCE DESCRIPTION: SEQ ID NO: 46:

GCTCTAGATT AATTCGCCTG ACCGGC                                    26
```